US011865104B2

(12) United States Patent
Maciejewski et al.

(10) Patent No.: US 11,865,104 B2
(45) Date of Patent: Jan. 9, 2024

(54) ANTITUMOR TET2 MODULATING COMPOUNDS

(71) Applicant: THE CLEVELAND CLINIC FOUNDATION, Cleveland, OH (US)

(72) Inventors: Jaroslaw Maciejewski, Cleveland, OH (US); Babal K. Jha, Cleveland, OH (US); James G. Phillips, Cleveland, OH (US); Thomas Radivoyevitch, Cleveland, OH (US); Yihong Guan, Cleveland, OH (US); Anand D. Tiwari, Cleveland, OH (US)

(73) Assignee: THE CLEVELAND CLINIC FOUNDATION, Cleveland, OH (US)

( * ) Notice: Subject to any disclaimer, the term of this patent is extended or adjusted under 35 U.S.C. 154(b) by 412 days.

(21) Appl. No.: 16/768,112

(22) PCT Filed: Nov. 29, 2018

(86) PCT No.: PCT/US2018/063069
§ 371 (c)(1),
(2) Date: May 29, 2020

(87) PCT Pub. No.: WO2019/108796
PCT Pub. Date: Jun. 6, 2019

(65) Prior Publication Data
US 2020/0306221 A1 Oct. 1, 2020

Related U.S. Application Data

(60) Provisional application No. 62/591,884, filed on Nov. 29, 2017.

(51) Int. Cl.
A61K 31/366 (2006.01)
A61P 35/02 (2006.01)
A61P 35/00 (2006.01)

(52) U.S. Cl.
CPC .......... *A61K 31/366* (2013.01); *A61P 35/00* (2018.01); *A61P 35/02* (2018.01)

(58) Field of Classification Search
CPC ......... A61K 31/366; A61P 35/00; A61P 35/02
See application file for complete search history.

(56) References Cited

U.S. PATENT DOCUMENTS 4,938,949 A 7/1990 Borch et al.
2012/0328518 A1* 12/2012 Graham .............. A61K 51/0489
514/121

FOREIGN PATENT DOCUMENTS

EP 2530068 A1 12/2012
WO 2010/087702 A1 8/2010
WO WO-2012163563 A1 * 12/2012 ............. C07C 55/02
WO 2016196962 A1 12/2016

OTHER PUBLICATIONS

Franck-Neumann et al. Stereospecific synthesis of cis pyrethroids using a carbanionic synthon. I. Gem-pyrazolenines. Tetrahedron 1987, 43, 845-852 (Year: 1987).*
Chataigner et al. Asymmetric Synthesis using a New Chiral β-Functionalized Allylboronate derived from endo-2-phenyi-exo-2,3-bornanediol: Preparation and Reactions with Aldehydes. Tetrahedron Lett. 1997, 38, 3719-3722 (Year: 1997).*
Helaine et al. Chemoenzymatic Synthesis of (4S)- and (4R)-4-Methyl-2-oxoglutaric Acids, Precursors of Glutamic Acid Analogues. Eur. J. Org. Chem. 1999, 3403-3406 (Year: 1999).*
Drioli et al. Chemoenzymatic synthesis of optically active 4-methyl-tetrahydro-5-oxo-2-furancarboxylic acids and esters. Tetrahedron: Asymmetry 2000, 11, 1353-1366 (Year: 2000).*
Chataigner et al. Enantioselective addition of β-functionalized allylboronates to aldehydes and aldimines. Stereocontrolled synthesis of α-methylene-γ-lactones and lactams. Tetrahedron 2008, 64, 2441-2455 (Year: 2008).*
Graham et al. Radiofluorinated Derivatives of 2-(Phosphonomethyl)pentanedioic Acid as Inhibitors of Prostate Specific Membrane Antigen (PSMA) for the Imaging of Prostate Cancer. J. Med. Chem. 2012, 55, 9510-9520 (Year: 2012).*
Liu et al. Structural Requirements of 2-Oxoglutaric Acid Analogues To Mimic Its Signaling Function. Org. Lett. 2013, 15, 4662-4665 (Year: 2013).*
Wang et al. Synthesis of Itaconic Acid Ester Analogues via Self-Aldol Condensation of Ethyl Pyruvate Catalyzed by Hafnium BEA Zeolites. ACS Catal. 2016, 6, 2739-2744 (Year: 2016).*
Breski et al. Engineering Biological C—H Functionalization Leads to Allele-Specific Regulation of Histone Demethylases. J. Am. Chem. Soc. 2016, 138, 13505-13508 (Year: 2016).*
Agger et al. Jmjd2/Kdm4 demethylases are required for expression of Il3ra and survival of acute myeloid leukemia cells. Genes & Dev. 2016, 30, 1278-1288. (Year: 2016).*
Cimmino et al. Restoration of TET2 Function Blocks Aberrant Self-Renewal and Leukemia Progression. Cell 2017, 170, 1079-1095. (Year: 2017).*
Helaine et al. Eur. J. Org. Chem. 1999, 12, 3403-3406 (Year: 1999).*
Drioli et al. Tetrahedron 2000, 11, 1353-1366 (Year: 2000).*

(Continued)

*Primary Examiner* — Amanda L. Aguirre
(74) *Attorney, Agent, or Firm* — TAROLLI, SUNDHEIM, COVELL & TUMMINO L.L.P.

(57) ABSTRACT

A method of treating cancer is described. The method includes administering a therapeutically effective amount of a TET2 activating compound or pharmaceutically acceptable salt thereof to a subject in need of treatment. The TET2 activating compounds are α-ketoglutarate derivatives. A method of treating or preventing cancer in a subject that includes the step of analyzing a biological sample to determine if cells of the biological sample exhibit a TET2 mutation in addition to administering a TET2 activator is also described.

7 Claims, 7 Drawing Sheets

Specification includes a Sequence Listing.

(56) References Cited

OTHER PUBLICATIONS

Liu et al. Org. Lett. 2011, 13, 2924-2927 (Year: 2011).*
Liu et al. Org. Lett. 2013, 15, 4662-4665 (Year: 2013).*
Kang, Han-Young, et al. "Synthesis of α-ketobutyrolactones and γ-hydroxy-α-keto acids." Bulletin of the Korean Chemical Society 24.12 (2003): 1819-1826.
Tiwari, Anand D., et al. "SAR insights into TET2 catalytic domain inhibition: Synthesis of 2-Hydroxy-4-Methylene-pentanedicarboxylates." Bioorganic & Medicinal Chemistry 39 (2021): 116141.
European Search Report for corresponding Application Serial No. 18821839.0-1112, dated Nov. 18, 2022, pp. 1-8.
Cimmino, Luisa, et al. "Restoration of TET2 function blocks aberrant self-renewal and leukemia progression." Cell 170.6 (2017): 1079-1095.
Zdzisinska, Barbara, Aleksandra Zurek, and Martyna Kandefer-Szerszen. "Alpha-ketoglutarate as a molecule with pleiotropic activity: well-known and novel possibilities of therapeutic use." Archivum immunologiae et therapiae experimentalis 65.1 (2017): 21-36.
PCT International Search Report and Written Opinion for corresponding International Application Serial No. PCT/US2018/063089, dated Apr. 23, 2019, pp. 1-19.
Morris LG, Chan TA. Therapeutic targeting of tumor suppressor genes. Cancer. May 1, 2015;121(9):1357-68. doi: 10.1002/cncr.29140. Epub Dec. 29, 2014. PMID: 25557041; PMCID: PMC4526158.
Radivoyevitch T, Loparo KA, Jackson RC, Sedwick WD. On systems and control approaches to therapeutic gain. BMC Cancer. Apr. 25, 2006;6:104. doi: 10.1186/1471-2407-6-104. PMID: 16638124; PMCID: PMC1484487.
Jankowska AM, Szpurka H, Tiu RV, Makishima H, Afable M, Huh J, O'Keefe CL, Ganetzky R, McDevitt MA, Maciejewski JP. Loss of heterozygosity 4q24 and TET2 mutations associated with myelodysplastic/myeloproliferative neoplasms. Blood. Jun. 18, 2009;113(25):6403-10. doi: 10.1182/blood-2009-02-205690. Epub Apr. 16, 2009. PMID: 19372255; PMCID: PMC2710933.
Tahiliani M, Koh KP, Shen Y, Pastor WA, Bandukwala H, Brudno Y, Agarwal S, Iyer LM, Liu DR, Aravind L, Rao A. Conversion of 5-methylcytosine to 5-hydroxymethylcytosine in mammalian DNA by MLL partner TET1. Science. May 15, 2009;324(5929):930-5. doi: 10.1126/science.1170116. Epub Apr. 16, 2009. PMID: 19372391; PMCID: PMC2715015.
Muramatsu H, Makishima H, Jankowska AM, Cazzolli H, O'Keefe C, Yoshida N, Xu Y, Nishio N, Hama A, Yagasaki H, Takahashi Y, Kato K, Manabe A, Kojima S, Maciejewski JP. Mutations of an E3 ubiquitin ligase c-Cbl but not TET2 mutations are pathogenic in juvenile myelomonocytic leukemia. Blood. Mar. 11, 2010;115(10):1969-75. doi: 10.1182/blood-2009-06-226340. Epub Dec. 11, 2009. PMID: 20008299; PMCID: PMC2837338.
Genovese G, Kähler AK, Handsaker RE, Lindberg J, Rose SA, Bakhoum SF, Chambert K, Mick E, Neale BM, Fromer M, Purcell SM, Svantesson O, Landén M, Höglund M, Lehmann S, Gabriel SB, Moran JL, Lander ES, Sullivan PF. Sklar P, Grönberg H, Hultman CM, McCarroll SA. Clonal hematopoiesis and blood-cancer risk inferred from blood DNA sequence. N Engl J Med. Dec. 25, 2014;371(26):2477-87. doi: 10.1056/NEJMoa1409405. Epub Nov. 26, 2014. PMID: 25426838; PMCID: PMC4290021.
Jaiswal S, Fontanillas P, Flannick J, Manning A, Grauman PV, Mar BG, Lindsley RC, Mermel CH, Burtt N, Chavez A, Higgins JM, Moltchanov V, Kuo FC, Kluk MJ, Henderson B, Kinnunen L, Koistinen HA, Ladenvall C, Getz G, Correa A, Banahan BF, Gabriel S, Kathiresan S, Stringham HM, McCarthy MI, Boehnke M, Tuomilehto J, Haiman C, Groop L, Atzmon G, Wilson JG, Neuberg D, Altshuler D, Ebert BL. Age-related clonal hematopoiesis associated with adverse outcomes. N Engl J Med. Dec. 25, 2014;371(26):2488-98. doi: 10.1056/NEJMoa1408617. Epub Nov. 26, 2014.
Steensma DP, Bejar R, Jaiswal S, Lindsley RC, Sekeres MA, Hasserjian RP, Ebert BL. Clonal hematopoiesis of indeterminate potential and its distinction from myelodysplastic syndromes. Blood. Jul. 2, 2015;126(1):9-16. doi: 10.1182/blood-2015-03-631747. Epub Apr. 3., 2015. PMID: 25931582; PMCID: PMC4624443.

Polin L, Valeriote F, White K, Panchapor C, Pugh S, Knight J, LoRusso P, Hussain M, Liversidge E, Peltier N, Golakoti T, Patterson G, Moore R, Corbett TH. Treatment of human prostate tumors PC-3 and TSU-PR1 with standard and investigational agents in SCID mice. Invest New Drugs. 1997;15(2):99-108. doi: 10.1023/a:1005856605726. PMID: 9220288.
Greenberg NM, DeMayo F, Finegold MJ, Medina D, Tilley WD, Aspinall JO, Cunha GR, Donjacour AA, Matusik RJ, Rosen JM. Prostate cancer in a transgenic mouse. Proc Natl Acad Sci U S A. Apr. 11, 1995;92(8):3439-43. doi: 10.1073/pnas.92.8.3439. PMID: 7724580; PMCID: PMC42182.
Haynes DA, Jones W, Samuel Motherwell WD. Occurrence of pharmaceutically acceptable anions and cations in the Cambridge Structural Database. J Pharm Sci. Oct. 2005;94(10):2111-20. doi: 10.1002/jps.20441. PMID: 16136575.
Fieser, Mary. Reagents for organic synthesis. vol. 3. John Wiley & Sons, 1971.
Katritzky, Alan R., et al., eds. Comprehensive organic functional group transformations. vol. 1. Elsevier, 1995.
Boit, Hans Günther, Friedrich Konrad Beilstein, and Reiner Luckenbach. Beilsteins Handbuch der Organischen Chemie. Springer, 1970.
Beer, Philip A., et al. "Two routes to leukemic transformation after a JAK2 mutation-positive myeloproliferative neoplasm." Blood 115.14 (2010): 2891-2900.
Zhao Z, Chen L, Dawlaty MM, Pan F, Weeks O, Zhou Y, Cao Z, Shi H, Wang J, Lin L, Chen S, Yuan W, Qin Z, Ni H, Nimer SD, Yang FC, Jaenisch R, Jin P, Xu M. Combined Loss of Tet1 and Tet2 Promotes B Cell, but Not Myeloid Malignancies, in Mice. Cell Rep. Nov. 24, 2015;13(8):1692-704. doi: 10.1016/j.celrep.2015.10.037. Epub Nov. 12, 2015. PMID: 26586431; PMCID: PMC4764044.
Hirsch CM, Nazha A, Kneen K, Abazeed ME, Meggendorfer M, Przychodzen BP, Nadarajah N, Adema V, Nagata Y, Goyal A, Awada H, Asad MF, Visconte V, Guan Y, Sekeres MA, Olinski R, Jha BK, LaFramboise T, Radivoyevitch T, Hafertach T, Maciejewski JP. Consequences of mutant TET2 on clonality and subclonal hierarchy. Leukemia. Aug. 2018:32(8):1751-1761. doi: 10.1038/s41375-018-0150-9. Epub May 24, 2018. PMID: 29795413.
Makishima H, Yoshizato I, Yoshida K, Sekeres MA, Radivoyevitch I, Suzuki A, Przychodzen B, Nagata Y, Meggendorfer M, Sanada M, Okuno Y, Hirsch C, Kuzmanovic T, Sato Y, Sato-Otsubo A, LaFramboise T, Hosono N, Shiraishi Y, Chiba K, Haferlach C, Kern W, Tanaka H, Shiozawa Y, Gómez-Seguí I, Husseinzadeh HD, Thota S, Guinta KM, Dienes B, Nakamaki T, Miyawaki S, Saunthararajah Y, Chiba S, Miyano S, Shih LY, Haferlach T, Ogawa S, Maciejewski JP. Dynamics of clonal evolution in myelodysplastic syndromes. Nat Genet. Feb. 2017;49(2):204-212.
Dawlaty MM, Breiling A, Le T, Barrasa MI, Raddatz G, Gao Q, Powell BE, Cheng AW, Faull KF, Lyko F, Jaenisch R. Loss of Tet enzymes compromises proper differentiation of embryonic stem cells. Dev Cell. Apr. 14, 2014;29(1):102-11. doi: 10.1016/j.devcel.2014.03.003. PMID: 24735881; PMCID: PMC4035811.
Hu L, Lu J, Cheng J, Rao Q, Li Z, Hou H, Lou Z, Zhang L, Li W, Gong W, Liu M, Sun C, Yin X, Li J, Tan X, Wang P, Wang Y, Fang D, Cui Q, Yang P. He C, Jiang H, Luo C, Xu Y. Structural insight into substrate preference for TET-mediated oxidation. Nature. Nov. 5, 2015;527(7576):118-22. doi: 10.1038/nature15713. Epub Oct. 28, 2015. PMID: 26524525.
Moran Crusio K, Reavie L, Shih A, Abdel-Wahab O, Ndiaye-Lobry D, Lobry C, Figueroa ME, Vasanthakumar A, Patel J, Zhao X, Perna F, Pandey S, Madzo J, Song C, Dai Q, He C, Ibrahim S, Beran M, Zavadil J, Nimer SD, Melnick A, Godley LA, Aifantis I, Levine RL. Tet2 loss leads to increased hematopoietic stem cell self-renewal and myeloid transformation. Cancer Cell. Jul. 12, 2011;20(1):11-24. doi: 10.1016/j.ccr.2011.06.001. Epub Jun. 30, 2011. PMID: 21723200; PMCID: PMC3194039.
Lindner D, Raghavan D. Intra-tumoural extra-cellular pH: a useful parameter of response to chemotherapy in syngeneic tumour lines. Br J Cancer. Apr. 21, 2009;100(8):1287-91. doi: 10.1038/sj.bjc.6605022. PMID: 19367285; PMCID: PMC2676543.
Li Z, Cai X, Cai CL, Wang J, Zhang W, Petersen BE, Yang FC, Xu M. Deletion of Tet2 in mice leads to dysregulated hematopoietic stem cells and subsequent development of myeloid malignancies.

(56) References Cited

OTHER PUBLICATIONS

Blood. Oct. 27, 2011;118(17):4509-18. doi: 10.1182/blood-2010-12-325241. Epub Jul. 29, 2011. PMID: 21803851; PMCID: PMC3952630.

Alaux S, Kusk M, Sagot E, Bolte J, Jensen AA, Bräuner-Osborne H, Gefflaut T, Bunch L. Chemoenzymatic synthesis of a series of 4-substituted glutamate analogues and pharmacological characterization at human glutamate transporters subtypes 1-3. J Med Chem. Dec. 15, 2005;48(25):7980-92. doi: 10.1021/jm050597z. PMID: 16335922.

Fernandes, Rodney A., and Dipali A. Chaudhari. "Development of the First Menthane-Based Chiral Bis (p-allylpalladium) Catalysis: Asymmetric Allylation of Imines." European Journal of Organic Chemistry 2012.10 (2012): 1945-1952.

Wong MK, Yu CW, Yuen WH, Yang D. Synthesis of alpha keto esters and amides via oxidative cleavage of cyanoketophosphoranes by dimethyldioxirane. J Org Chem. May 18, 2001;66(10):3606-9. doi: 10.1021/jo0015974. PMID: 11348154.

Liu X, Chen H, Laurini E, Wang Y, Dal Col V, Posocco P, Ziarelli F, Fermeglia M, Zhang CC, Pricl S, Peng L. 2-difluoromethylene 4-methylenepentanoic acid, a paradoxical probe able to mimic the signaling role of 2-oxoglutanic acid in cyanobacteria. Org Lett. Jun. 3, 2011;13(11):2924-7. doi: 10.1021/ol2009544. Epub May 5, 2011. PMID: 21545161.

\* cited by examiner

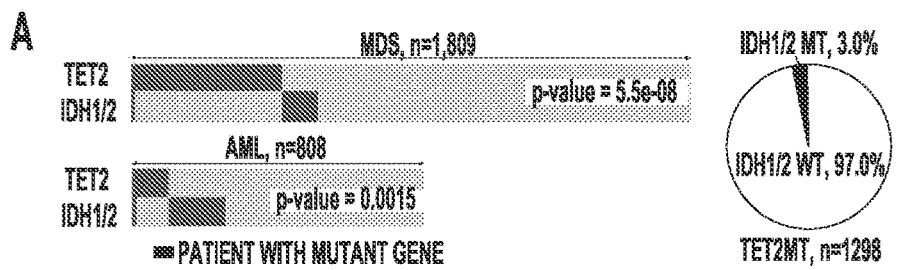
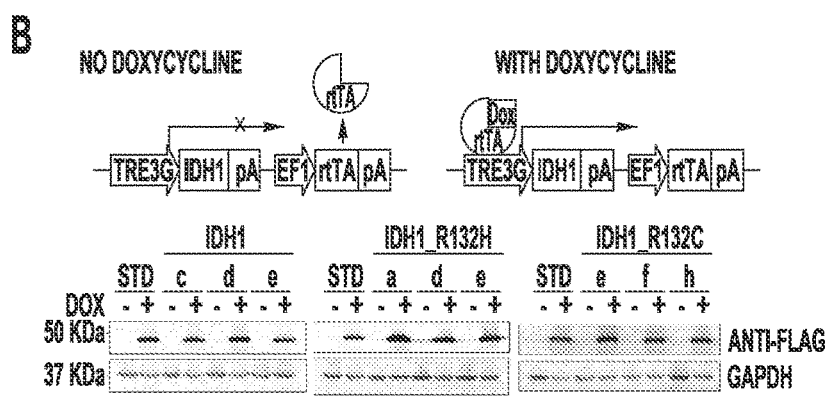
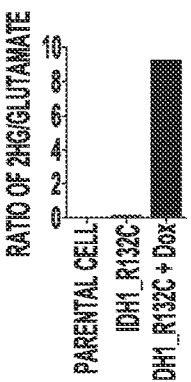
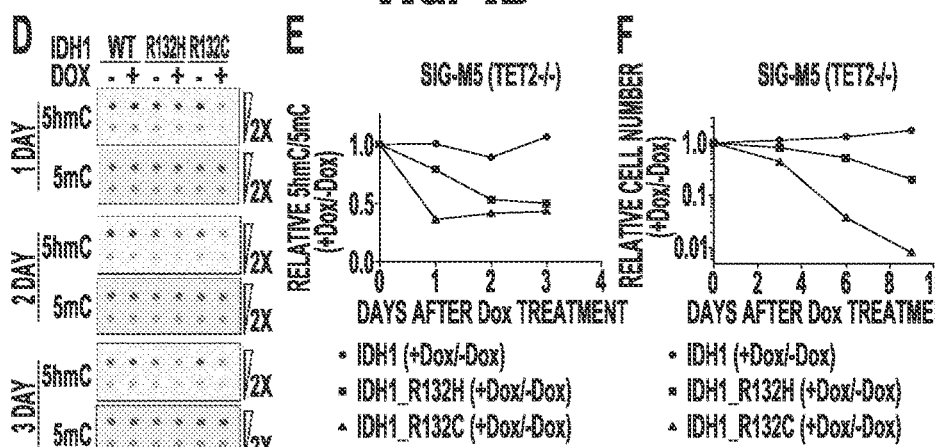
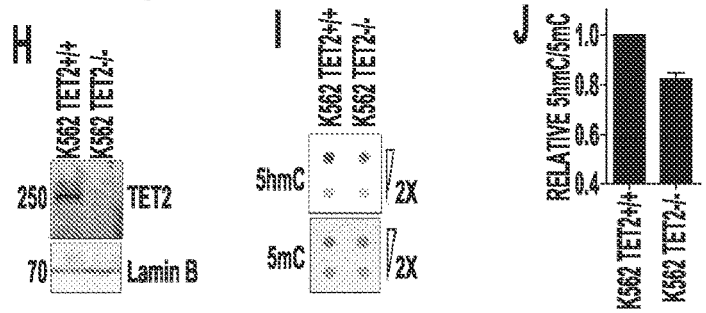
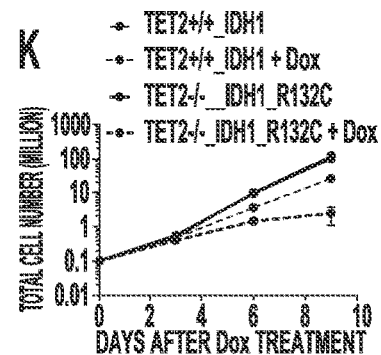

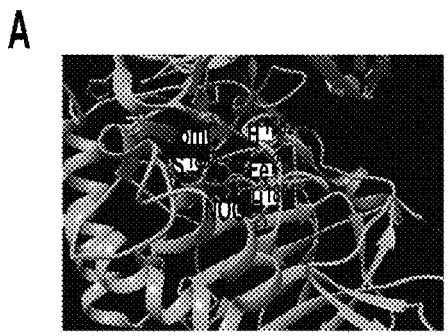
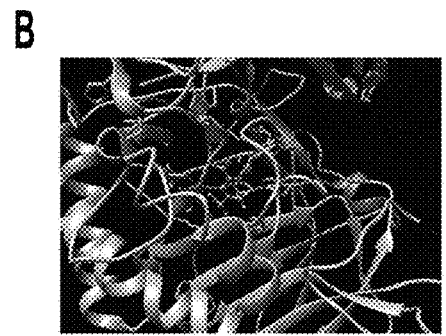
FIG. 2A  FIG. 2B
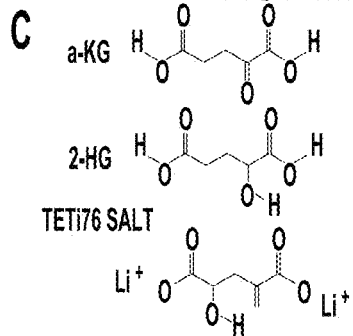
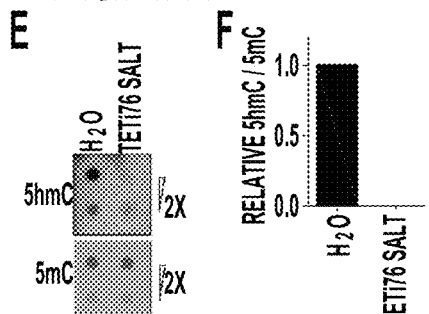
FIG. 2C  FIG. 2D  FIG. 2E  FIG. 2F
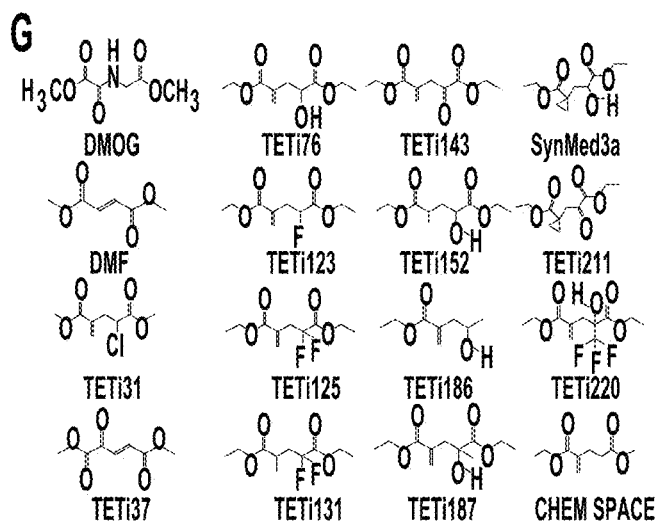
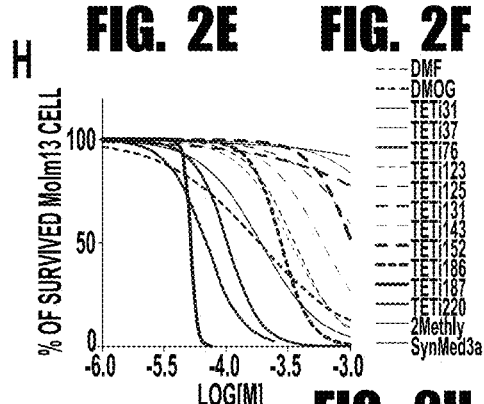
FIG. 2G  FIG. 2H
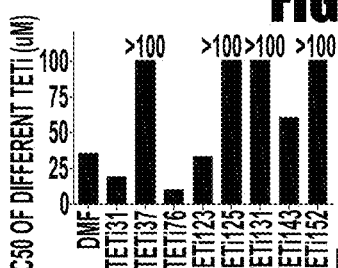
FIG. 2I
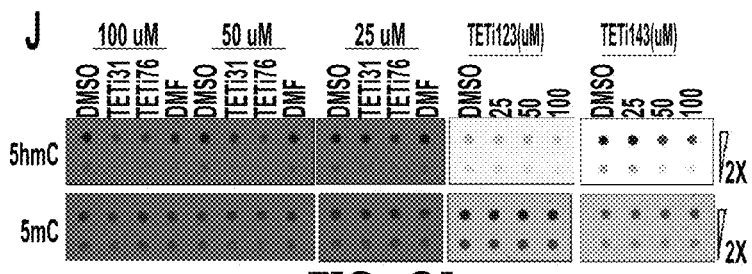
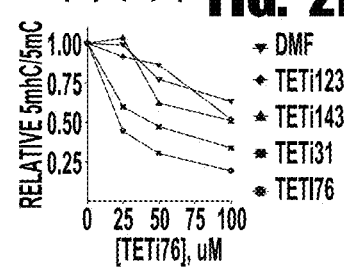
FIG. 2J  FIG. 2K

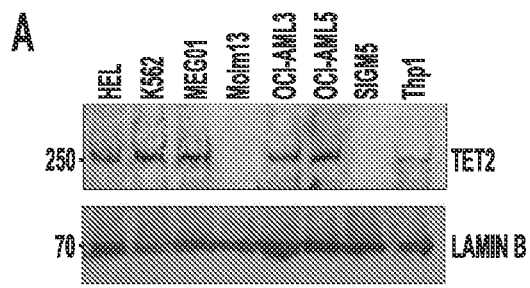
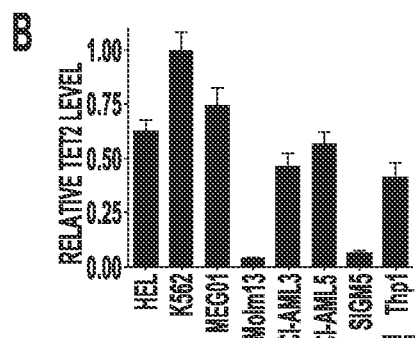
FIG. 3A
FIG. 3B
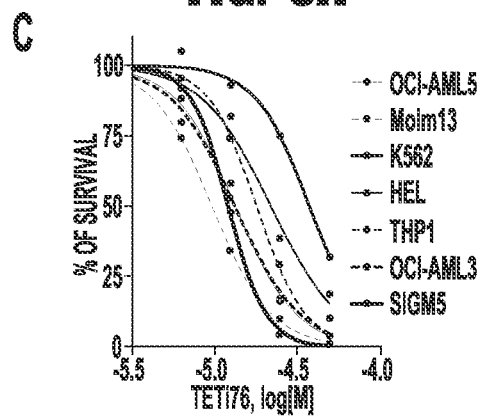
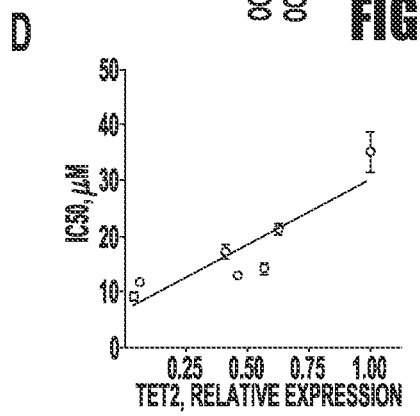
FIG. 3C
FIG. 3D
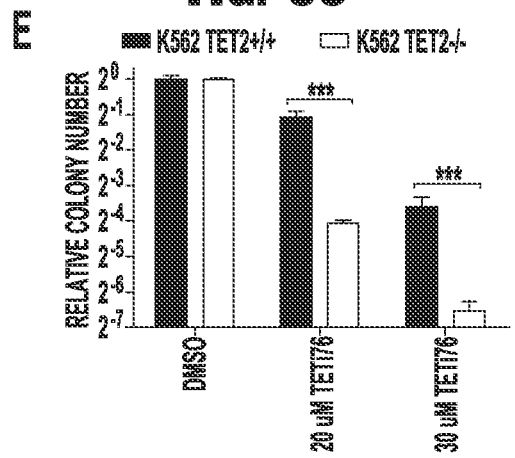
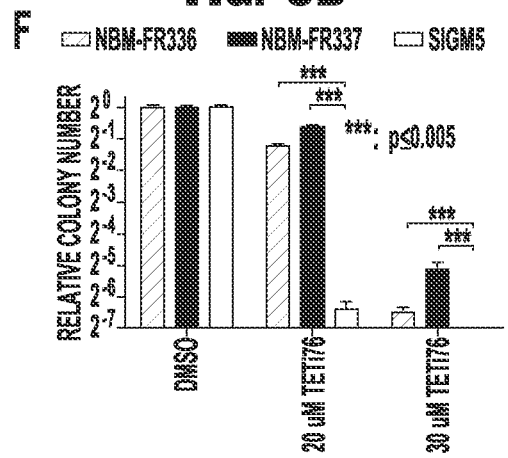
FIG. 3E
FIG. 3F
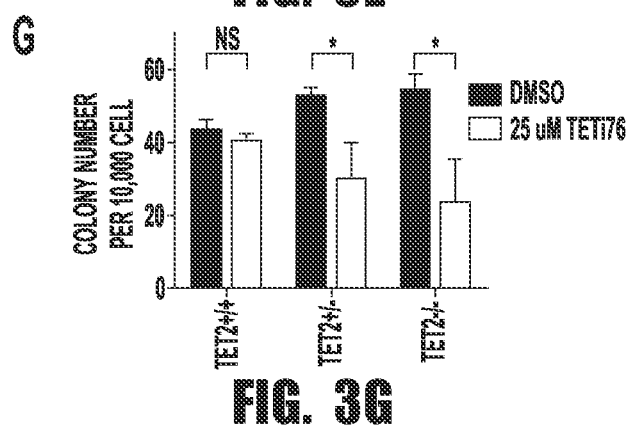
FIG. 3G

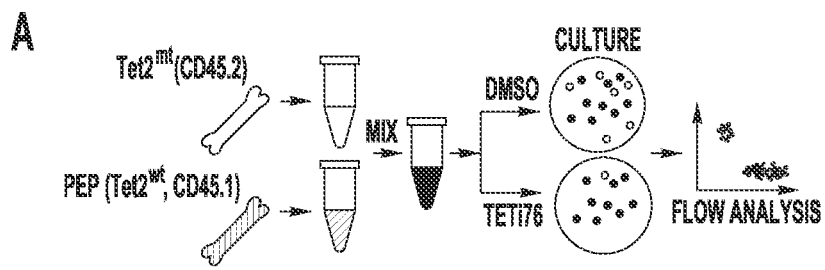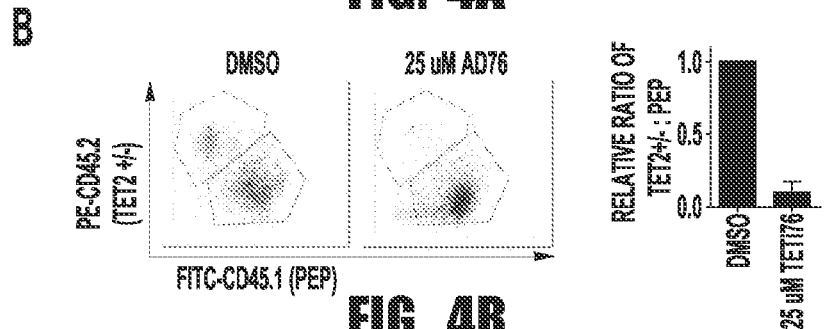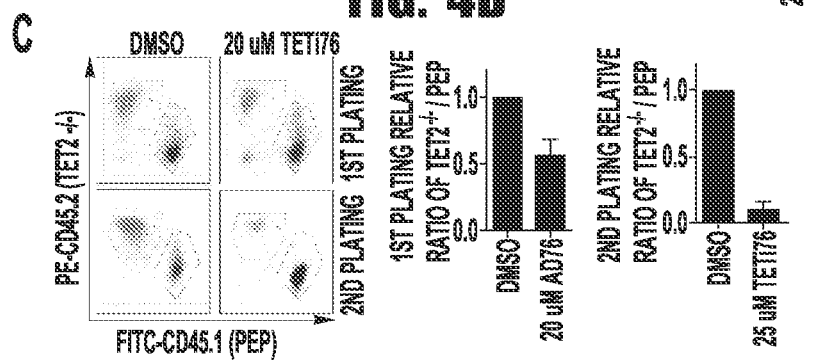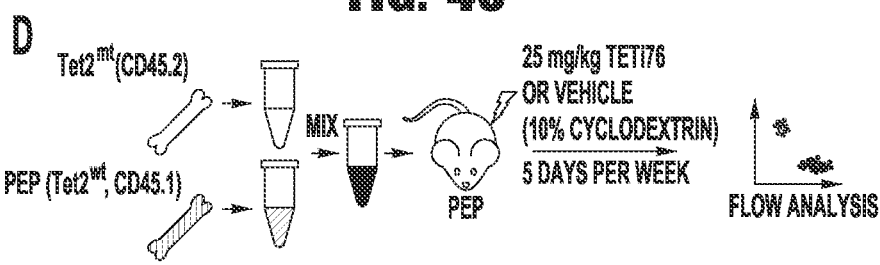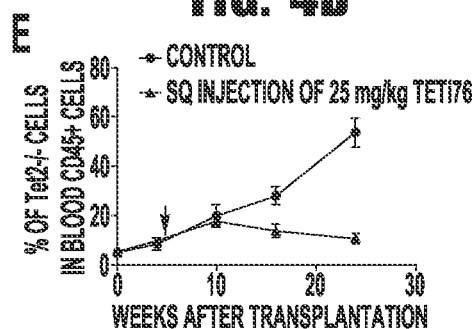

A

| | | |
|---|---|---|
| Q6N021 TET2_HUMAN | 1323 | ESHLQNLSTLMAPTYKKLAPDAYNNQIEYEHRAPECRLGLKEGRPFSGVTACLDFCAHAH |
| Q8NFU7 TET1_HUMAN | 1613 | EDNLQSLATRLAPIYKQYAPVAYQNQVEYENVARECRLGSKEGRPFSGVTACLDFCAHPH |
| O43151 TET3_HUMAN | 883 | RKSFQDLATEVAPLYKRLAPQAYQNQVTNEEIAIDCRLGLKEGRPFAGVTACMDFCAHAH |
| | | . .  * *  * **  * * *  ** * ::  *.  *   :**  **::*** * |
| Q6N021 TET2_HUMAN | 1383 | RDLHNMQNGSTLVCTLTREDNREFGGKPEDEQLHVLPLYKVSDVDEFGSVEAQEEKKRSG |
| Q8NFU7 TET1_HUMAN | 1673 | RDIHNMNNGSTWCTLTREDNRSLGVIPQDEQLHVLPLYKLSDTDEFGSKEGMEAKIKSG |
| O43151 TET3_HUMAN | 943 | KDQHNLYNGCTWCTLTKEDNRCVGKIPEDEQLHVLPLYKMANTDEFGSEENQNAKVGSG |
| | | :*  : .*:***:**  .*   *:*********:;.*** *   :* ** |
| Q6N021 TET2_HUMAN | 1755 | EHHSPSHIIHNYSAAPGMFNSSLHALHLQNKENDMLSHTANGLSKMLPALNH------DR---- |
| Q8NFU7 TET1_HUMAN | 1939 | PNHQPSFLTSP...................QQLASSPMEEDE-............... |
| O43151 TET3_HUMAN | 1389 | ALAGPSLTEKPWALGAGDFNSALKGSPGF----QDKLWNPMKGEEGRIPAAGASQLDRAWQ |
| | |     **                           :*   .                 |
| Q6N021 TET2_HUMAN | 1809 | ........TACVQGGLH----KLSD----ANGQ......EKQPLALVQ- -GVASGAEDNOEV |
| Q8NFU7 TET1_HUMAN | 1962 | ................QHSEADEPPSDEPLSDDPLSPAEEKLPHIDEY |
| O43151 TET3 HUMAN | 1446 | SFGLPLGSSEKLFGALKSEEKLWDPFSLEEGPAEEPPSKGAVKEEK--GGGGAEEEEEEL |
| | |                            . .    . .  :              . :* |
| Q6N021 TET2_HUMAN | 1847 | WSDSEQSFLDPDIGGVAVAPTHGSILIECAKRELHATTPLKNPNRNHPTRISLVFYQHKS |
| Q8NFU7 TET1_HUMAN | 1994 | WSDSEHIFLDANIGGVAIAPAHGSVLIECARREIHATTPVEHPNRNHPTRISLVFYQHKN |
| O43151 TET3_HUMAN | 1504 | WSDSEHNFLDENIGGVAVAPAHGSILIECARRELHATTPLKKPNRCHPTRISLVFYQHKN |
| | | ***:  *  :***::*:*;*:;*:; :*******. |
| Q6N021 TET2_HUMAN | 1907 | MNEPKHGLALWEAKMAEKA REKEEECEKYGPDYVPQKSHGKKVKREP---AEPHETS |
| Q8NFU7 TET1_HUMAN | 2054 | LNKPQHGFELNKIKFEAKEAKNKKMKAS........EQK.......DQAANEGPEQSS |
| O43151 TET3 HUMAN | 1564 | INQPNHGLALWEAKMKQLAERARARQEEAARLGLGQQEAKIYGKKRKWGGTWAEPQQKE |
| | | :*;*;** *  *.*:  .    :  .    :          *       *.::. |
| Q6N021 TET2_HUMAN | 1961 | EPTYLRFIKSLAERTMSVTTDSTVTTSPYAFTRVTGPYNRYI |
| Q8NFU7 TET1_HUMAN | 2097 | E- -VNELNQIPSHKALTLTHDNWTVSPYALTHVAGPYNHWV |
| O43151 TET3 HUMAN | 1624 | KKG.....WPTRQALAVPTDSAVTVSSYAYTKVTGPYSRWI |
| | |    :         *.. ***.* .**** :;*;**;;.:: |

Consensus binding site for known pseudo substrate NOG (A) and TETi (B). (C) The catalytic residues among TET proteins are highly conserved. Residues H1382, S1898 and H1801 interacting with TETi are identically positioned in All TETs.

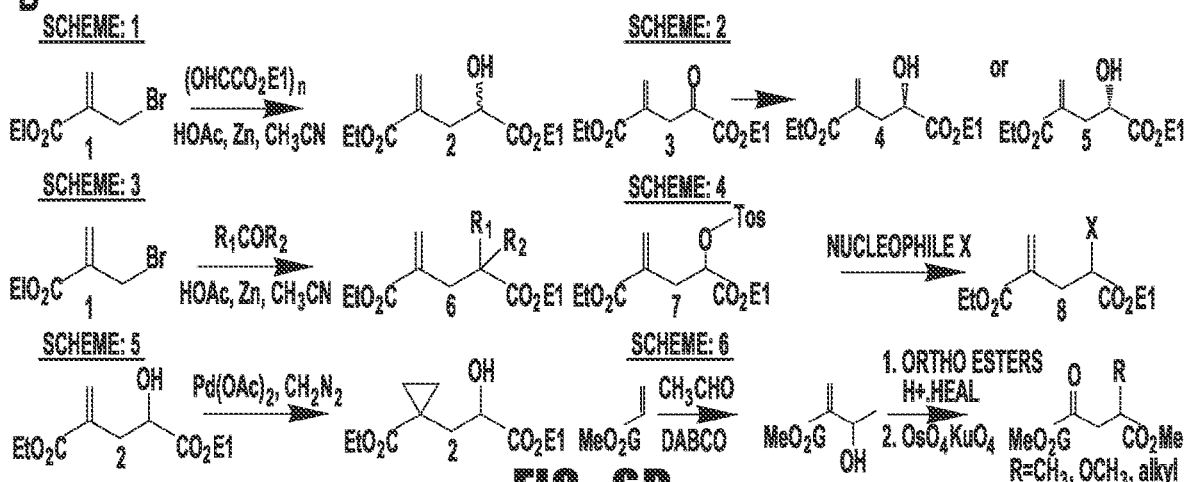

X = H, CH$_3$, F, CF$_3$, CH$_2$F, CYCLOPROPYL    & R = COOH, CONH2, OH, CF$_3$

SEQUENCE LISTING

```
<160> NUMBER OF SEQ ID NOS: 3

<210> SEQ ID NO 1
<211> LENGTH: 318
<212> TYPE: PRT
<213> ORGANISM: Homo sapiens

<400> SEQUENCE: 1

Glu Asp Asn Leu Gln Ser Leu Ala Thr Arg Leu Ala Pro Ile Tyr Lys
1               5                   10                  15

Gln Tyr Ala Pro Val Ala Tyr Gln Asn Gln Val Glu Tyr Glu Asn Val
            20                  25                  30

Ala Arg Glu Cys Arg Leu Gly Ser Lys Glu Gly Arg Pro Phe Ser Gly
        35                  40                  45

Val Thr Ala Cys Leu Asp Phe Cys Ala His Pro His Arg Asp Ile His
    50                  55                  60

Asn Met Asn Asn Gly Ser Thr Val Val Cys Thr Leu Thr Arg Glu Asp
65                  70                  75                  80

Asn Arg Ser Leu Gly Val Ile Pro Gln Asp Glu Gln Leu His Val Leu
                85                  90                  95

Pro Leu Tyr Lys Leu Ser Asp Thr Asp Glu Phe Gly Ser Lys Glu Gly
            100                 105                 110
```

-continued

Met Glu Ala Lys Ile Lys Ser Gly Pro Asn His Gln Pro Ser Phe Leu
            115                 120                 125

Thr Ser Pro Gln Asp Leu Ala Ser Ser Pro Met Glu Glu Asp Glu Gln
130                 135                 140

His Ser Glu Ala Asp Glu Pro Pro Ser Asp Glu Pro Leu Ser Asp Asp
145                 150                 155                 160

Pro Leu Ser Pro Ala Glu Glu Lys Leu Pro His Ile Asp Glu Tyr Trp
                165                 170                 175

Ser Asp Ser Glu His Ile Phe Leu Asp Ala Asn Ile Gly Gly Val Ala
            180                 185                 190

Ile Ala Pro Ala His Gly Ser Val Leu Ile Glu Cys Ala Arg Arg Glu
        195                 200                 205

Leu His Ala Thr Thr Pro Val Glu His Pro Asn Arg Asn His Pro Thr
    210                 215                 220

Arg Leu Ser Leu Val Phe Tyr Gln His Lys Asn Leu Asn Lys Pro Gln
225                 230                 235                 240

His Gly Phe Glu Leu Asn Lys Ile Lys Phe Glu Ala Lys Glu Ala Lys
                245                 250                 255

Asn Lys Lys Met Lys Ala Ser Glu Gln Lys Asp Gln Ala Ala Asn Glu
            260                 265                 270

Gly Pro Glu Gln Ser Ser Glu Val Asn Glu Leu Asn Gln Ile Pro Ser
        275                 280                 285

His Lys Ala Leu Thr Leu Thr His Asp Asn Val Val Thr Val Ser Pro
    290                 295                 300

Tyr Ala Leu Thr His Val Ala Gly Pro Tyr Asn His Trp Val
305                 310                 315

<210> SEQ ID NO 2
<211> LENGTH: 368
<212> TYPE: PRT
<213> ORGANISM: Homo sapiens

<400> SEQUENCE: 2

Glu Ser His Leu Gln Asn Leu Ser Thr Leu Met Ala Pro Thr Tyr Lys
1               5                   10                  15

Lys Leu Ala Pro Asp Ala Tyr Asn Asn Gln Ile Glu Tyr Glu His Arg
            20                  25                  30

Ala Pro Glu Cys Arg Leu Gly Leu Lys Glu Gly Arg Pro Phe Ser Gly
        35                  40                  45

Val Thr Ala Cys Leu Asp Phe Cys Ala His Ala His Arg Asp Leu His
    50                  55                  60

Asn Met Gln Asn Gly Ser Thr Leu Val Cys Thr Leu Thr Arg Glu Asp
65                  70                  75                  80

Asn Arg Glu Phe Gly Gly Lys Pro Glu Asp Glu Gln Leu His Val Leu
                85                  90                  95

Pro Leu Tyr Lys Val Ser Asp Val Asp Glu Phe Gly Ser Val Glu Ala
            100                 105                 110

Gln Glu Glu Lys Lys Arg Ser Gly Glu His His Ser Pro His Ile
        115                 120                 125

Ile His Asn Val Ser Ala Ala Pro Gly Met Phe Asn Ser Ser Leu His
    130                 135                 140

Ala Leu His Leu Gln Asn Lys Glu Asn Asp Met Leu Ser His Thr Ala
145                 150                 155                 160

Asn Gly Leu Ser Lys Met Leu Pro Ala Leu Asn His Asp Arg Thr Ala
                165                 170                 175

```
Cys Val Gln Gly Gly Leu His Lys Leu Ser Asp Ala Asn Gly Gln Glu
            180                 185                 190

Lys Gln Pro Leu Ala Leu Val Gln Gly Val Ala Ser Gly Ala Glu Asp
        195                 200                 205

Asn Asp Glu Val Trp Ser Asp Ser Glu Gln Ser Phe Leu Asp Pro Asp
    210                 215                 220

Ile Gly Gly Val Ala Val Ala Pro Thr His Gly Ser Ile Leu Ile Glu
225                 230                 235                 240

Cys Ala Lys Arg Glu Leu His Ala Thr Thr Pro Leu Lys Asn Pro Asn
                245                 250                 255

Arg Asn His Pro Thr Arg Ile Ser Leu Val Phe Tyr Gln His Lys Ser
            260                 265                 270

Met Asn Glu Pro Lys His Gly Leu Ala Leu Trp Glu Ala Lys Met Ala
        275                 280                 285

Glu Lys Ala Arg Glu Lys Glu Glu Cys Glu Lys Tyr Gly Pro Asp
    290                 295                 300

Tyr Val Pro Gln Lys Ser His Gly Lys Lys Val Lys Arg Glu Pro Ala
305                 310                 315                 320

Glu Pro His Glu Thr Ser Glu Pro Thr Tyr Leu Arg Phe Ile Lys Ser
                325                 330                 335

Leu Ala Glu Arg Thr Met Ser Val Thr Thr Asp Ser Thr Val Thr Thr
            340                 345                 350

Ser Pro Tyr Ala Phe Thr Arg Val Thr Gly Pro Tyr Asn Arg Tyr Ile
        355                 360                 365

<210> SEQ ID NO 3
<211> LENGTH: 392
<212> TYPE: PRT
<213> ORGANISM: Homo sapiens

<400> SEQUENCE: 3

Arg Lys Ser Phe Gln Asp Leu Ala Thr Glu Val Ala Pro Leu Tyr Lys
1               5                   10                  15

Arg Leu Ala Pro Gln Ala Tyr Gln Asn Gln Val Thr Asn Glu Glu Ile
            20                  25                  30

Ala Ile Asp Cys Arg Leu Gly Leu Lys Glu Gly Arg Pro Phe Ala Gly
        35                  40                  45

Val Thr Ala Cys Met Asp Phe Cys Ala His Ala His Lys Asp Gln His
    50                  55                  60

Asn Leu Tyr Asn Gly Cys Thr Val Val Cys Thr Leu Thr Lys Glu Asp
65                  70                  75                  80

Asn Arg Cys Val Gly Lys Ile Pro Glu Asp Glu Gln Leu His Val Leu
                85                  90                  95

Pro Leu Tyr Lys Met Ala Asn Thr Asp Glu Phe Gly Ser Glu Glu Asn
            100                 105                 110

Gln Asn Ala Lys Val Gly Ser Gly Ala Leu Ala Gly Pro Ser Leu Thr
        115                 120                 125

Glu Lys Pro Trp Ala Leu Gly Ala Gly Asp Phe Asn Ser Ala Leu Lys
    130                 135                 140

Gly Ser Pro Gly Phe Gln Asp Lys Leu Trp Asn Pro Met Lys Gly Glu
145                 150                 155                 160

Glu Gly Arg Ile Pro Ala Ala Gly Ala Ser Gln Leu Asp Arg Ala Trp
                165                 170                 175

Gln Ser Phe Gly Leu Pro Leu Gly Ser Ser Glu Lys Leu Phe Gly Ala
```

-continued

```
                180                 185                 190
Leu Lys Ser Glu Glu Lys Leu Trp Asp Pro Phe Ser Leu Glu Glu Gly
        195                 200                 205

Pro Ala Glu Glu Pro Pro Ser Lys Gly Ala Val Lys Glu Lys Gly
        210                 215                 220

Gly Gly Gly Ala Glu Glu Glu Glu Glu Leu Trp Ser Asp Ser Glu
225                 230                 235                 240

His Asn Phe Leu Asp Glu Asn Ile Gly Gly Val Ala Val Ala Pro Ala
                245                 250                 255

His Gly Ser Ile Leu Ile Glu Cys Ala Arg Arg Glu Leu His Ala Thr
                260                 265                 270

Thr Pro Leu Lys Lys Pro Asn Arg Cys His Pro Thr Arg Ile Ser Leu
        275                 280                 285

Val Phe Tyr Gln His Lys Asn Leu Asn Gln Pro Asn His Gly Leu Ala
        290                 295                 300

Leu Trp Glu Ala Lys Met Lys Gln Leu Ala Glu Arg Ala Arg Ala Arg
305                 310                 315                 320

Gln Glu Glu Ala Ala Arg Leu Gly Leu Gly Gln Gln Glu Ala Lys Leu
                325                 330                 335

Tyr Gly Lys Lys Arg Lys Trp Gly Gly Thr Val Val Ala Glu Pro Gln
                340                 345                 350

Gln Lys Glu Lys Lys Gly Val Val Pro Thr Arg Gln Ala Leu Ala Val
                355                 360                 365

Pro Thr Asp Ser Ala Val Thr Val Ser Ser Tyr Ala Tyr Thr Lys Val
        370                 375                 380

Thr Gly Pro Tyr Ser Arg Trp Ile
385                 390
```

ANTITUMOR TET2 MODULATING COMPOUNDS

CROSS-REFERENCE TO RELATED APPLICATIONS

This application claims priority to U.S. Provisional Patent Application No. 62/591,884, filed on Nov. 29, 2017, which is hereby incorporated by reference in its entirety.

SEQUENCE LISTING

The instant application contains a Sequence Listing which has been submitted electronically in ASCII format and is hereby incorporated by reference in its entirety. Said ASCII copy, created on Nov. 29, 2018, is named CCF-027130WO ORD SEQUENCE LISTING_ST25 and is 9,624 bytes in size.

BACKGROUND

Myelodysplastic syndrome (MDS), a disease of hematopoietic stem and progenitor cells (HSPC), is characterized by dysplasia, cytopenias and leukemic evolution. MDS and similar conditions including MDS/myeloproliferative neoplasms (MDS/MPN) and secondary acute myelogenous leukemia (sAML) may show overlapping histomorphologic features and share chromosomal aberrations and mutations. MDS is a disease of predominantly the elderly. It is thus often accompanied by chronic comorbidities and as a result, high mortality rates. Due to increasing life expectancy in the United States, the incidence and socioeconomic importance of MDS is growing. There are ~20,000 cases/year, or ~6/$10^5$ per year in the US. The urgent need for expanded research in MDS is founded in the fact that the therapeutic spectrum for MDS patients is limited to a few FDA-approved drugs of which none has shown curative potential. More rational approaches to MDS treatment development need to leverage new diagnostic gene mutation biomarkers. The most commonly mutated gene in MDS is Tet methylcytosine dioxygenase 2 (TET2), so it is rational to focus on it as our highest priority. TET2 mutations occur early in MDS development and have not been a subject of drug development despite having potential for therapeutic targeting. Morris L G, Chan T A., Cancer, 121(9):1357-68 (2015); Radivoyevitch et al., BMC Cancer, 6:104 (2006); Jankowska et al., Blood, 113(25):6403-6410 (2009).

TET1, TET2 and TET3 are $Fe^{2+}$ and α-ketoglutarate (α-KG) dependent DNA-dioxygenases that catalyze the oxidation of 5-methylcytosine (mC) to 5-hydroxymethylcytosine (hmC), this to 5-formylcytosine (fC), and this to 5-carboxylcytosine (caC). Ponnaluri et al., Biochem Biophys Res Commun., 436(2):115-20 (2013). This results in DNA demethylation either actively, by base excision repair of fC and caC, or passively, via replication, due to DNA methyltransferase's inability to recognize/read hmC. The resulting DNA demethylation increases gene transcription. Loss-of-function mutations in TET2 associate with hematopoietic stem and progenitor cell (HSPC) expansion (Tahiliani et al., Science, 324(5929):930-5 (2009)) and myeloid & lymphoid malignancies. Jankowska et al., Blood, 113(25):6403-10 (2009). Diminished TET activity may also be a feature in melanoma, glioblastoma and breast cancer, wherein it seems to correlate with advanced disease and poor survival. Huang et al., Trends Genet., 30(10):464-74 (2014). Somatic mutations in TET2 ($TET2^{MT}$) are one of the most common genetic defects in hematologic malignancies (Muramatsu et al., Blood, 115(10):1969-75 (2010)), including myelodysplastic syndrome (MDS), myeloproliferative neoplasm (MPN), and acute myeloid leukemia (AML). In chronic myelomonocytic leukemia (CMML) the prevalence of $TET2^{MT}$ approaches 50% with almost half being biallelic alterations. $TET2^{MT}$ are ancestral in ~50% of cases and their incidence increases with age. Genovese et al., N Engl J Med., 371(26):2477-87 (2014).

More than 70% of MDS patients >80 years old carry $TET2^{MT}$. $TET2^{MT}$ are also found in aging healthy controls, in whom their presence, now referred as to clonal hematopoiesis of indeterminate potential (CHIP), was associated with a subsequent risk of developing hematological malignancies. Jaiswal et al., N Engl J Med., 371(26):2488-2498 (2014). The frequency of TET2 mutations in healthy elderly increases from ~5% in 60-80 year olds to ~10% in 80-90 year olds to ~25% in >90 y olds. Steensma et al., Blood, 126(1):9-16 (2015). This finding, and higher frequencies of $TET2^{MT}$ in myeloid malignancies with stronger age-dependencies (i.e. CMML and MDS), suggests that TET2 is a key player in their pathogenesis. Its ancestral nature, supported by its prevalence in CHIP, suggests that targeting this mutation could disrupt the clone at its foundation, and thus have long-term benefits, if the clone is still dependent upon it. Its presence at the earliest stages of cancer evolution further suggests that it is a rational target for preventive strategies, with very high certainty, since the clone in such stages is likely to be dependent on TET2 loss.

Targeting TET2 could have a broad impact on both asymptomatic $TET2^{MT}$ CHIP cases and patients with fully developed, clinically-diagnosed hematological malignancies. Although strategies targeting early hits could potentially reverse an essential pathogenic step rather than merely peel back a last-hit to eliminate a sub-clone, to date, no such therapies have been developed for $TET2^{MT}$ neoplasia, though some recent studies have suggested that vitamin C (vitC) could be effective in some $TET2^{MT}$ cases. Generating α-KG analogs could have implications beyond TET2, as they may also target myeloid cancers with mutations in IDH1/2 and dioxygenases that demethylate histones such as KDM6A. Accordingly, there is a need for developing novel therapeutics that target TET2MT MDS and related neoplasms.

SUMMARY OF THE INVENTION

The development of an entirely novel strategy for targeted drug therapy is described herein, based on the principle of up-modulation of the function of the unaffected allele in cases with heterozygous hypomorphic mutations in tumor suppressor genes coding for proteins with the enzymatic activity. Specifically, the invention targets important dioxygenase enzyme classes which act indirectly as demethylases for both DNA and histones. The therapeutic significance of the proposed approach is founded in the importance of genes TET2 and UTX1, frequently affected by somatic mutations in myeloid neoplasia. For instance, among dioxygenases, TET2 is mutated in up to 20% of patients with myelodysplastic syndrome (MDS). MDS/myeloproliferative overlap syndrome (MDS/MPN) and in 5% of acute myelogenous leukemia (AML). UTX is another important dioxygenase mutated in an additional 5% of myeloid neoplasia. Myeloid neoplasia affected by these mutations would constitute a rational target for substrate agonists and the presence of the mutations would be a basis for the development of companion analytics. There are no targeted therapeutics for these mutations and due to poor outcomes of current therapies there is a medically urgent need to develop effective therapeutics for these mutations and due to poor outcomes of current therapies there is a medically urgent need to develop effective therapeutics. The invention will therefore have a vast translational impact not only on myeloid cancers but also on bladder cancers, wherein KDM6A (i.e. UTX) is the most common mutation.

Dioxygenases such as TET2 and UTX effectively demethylate (either DNA or K237 mark on histone H3) via a hydroxylation step that utilizes α-KG as a substrate in the presence of VitC. Somatic mutations are mostly heterozygous (except for UTX in males because UTX is located on the X chromosome) and thus hypomorphic heterozygous mutations lead to deficient function. Whether missense, stop codon or frame shift mutations, we have conceptualized that the activity of the remaining healthy alleles can be increased to offset the loss of one allele. This effect will be produced by optimizing the enzymatic function by improved substrates whose structures have been designed based on the computational modeling tested in cell free systems with purified enzyme in wild type form mixed 1:1 with functionally inactive variant and tested in vivo using appropriate methylation assays.

TET is a dioxygenase that hydroxylates Me-CpG (MC) to HOMe-CpG (HMC) which prevents maintenance methylation and/or induces MC elimination via base excision repair. Tahiliani et al., Science, 324(5929):930-5 (2009). MC shut genes off and poises for C>T transitions via cytidine deamination. For hydroxylation, TET2 requires a radical equivalent to abstract the hydrogen atom from MC. It obtains this by cleaving the 0-0 bond of $O_2$. For this, it uses 2 electrons from α-KG and 2, in two separate single-electron transfers (to produce a radical intermediate), from vitC. Our results with purified TET2 supports vitC increasing the enzymatic activity of wild-type TET2, unhindered by the presence of $TET2^{MT}$.

The inventors propose that if dioxygenase activity of the wild type allele can be up-modulated, the haploinsufficiency created by the mutation can be overcome, i.e., that increasing TET2 activity to overcome its haploinsufficiency will protract onset of clinical disease or be effective in treatment of diagnosed malignant $TET2^{MT}$ neoplasm. To advance this theory, TET2 turbosubstrates (FIG. 2G) and VitC were generated and tested in cell free systems and in vivo α-KG alone. Effects of these agents will be tested in preventative and therapeutic modes to determine not only clinical outcomes but also correlative molecular parameters such as rates of subclone evolution.

The inventors analyzed a very large cohort of 5,000 patients with myeloid neoplasms and have identified 1200 somatic mutant cases with 1680 mutations. The size of the cohort enabled a more intricate analysis of the distribution of mutations among disease subentities and determination of the rate of hemizygous homozygous and biallelic mutations (30% of all mutant cases). Analysis of the mutations showed that 80% were frame shifts leading to various truncations and of 20% of missense mutations 88% were located proximal to the active site. Of importance for the proposed studies the configuration of biallelic mutations included 2 frame shift alterations 110/557 (20%), while 2 missense mutations were biallelic in 7% of cases. Similarly, only 11% of mutant cases showed homo/hemizygous TET2 truncation mutations. Using exome sequencing on 350 cases, the clonal hierarchy of the TET2 mutations was analyzed. $TET2^{MT}$ cases showed highest VAFs in 65% of patients; in these patients $TET^{MT}$ are ancestral. Taken together, TET2 mutations as a target for rational drug development are present in a significant fraction of patients with myeloid neoplasms. Most TET2 mutations are heterozygous or biallelic involving 2 missense mutations or at least one missense mutation and thus the approach of increasing the activity of the remaining allele to alleviate the effects of mutation may affect most of the cells in the malignant clone. UTX mutations were found to be present in additional 5% of patients with myeloid neoplasia. In addition, enhanced α-KG-substrate may find therapeutic utility in 10% of MDS patients with IDH2 or IDH1 mutations and in 15% of patients with AML.

Based on the structure of a surrogate of α-KG in complex with TET2, the inventors have performed in silico docking analyses of α-KG and various TS analogs in the catalytic site of TET2WT. These studies focused initially on syntheses of derivatives with informative modifications at C-4, which can be modified with substituents that make the TX more efficient and specific for TET2. Various C4 derivatives will be synthesized, including C3-C4 alkenyl and alkynyl derivatives according to an established synthetic scheme (Jankowska et al., Blood, 113(25):6403-10 (2009)), the C-4 methyl analog has been prepared as a dimethylester for in vitro analyses (see below). The inventors determined if a better binding substrate is a better activator in a thermophoresis based binding assay coupled using their well-established enzyme activity assay.

To determine if the effects of turbosubstrates w/wo VitC can be measured, the inventors engineered TET2 knockdown models using retroviral shRNA transduction. In preliminary experiments TET2 knockdown cell lines were generated and cultured in the presence of VitC, DMKG, TS and their combinations. The inventors also knocked down TET2 in CD34+ cells obtained from healthy controls. In MOLM and K562 TET2 knockdown cells, VitC and DMKG yield differential and dose-dependent inhibitory effects compared to cells with scrambled shRNA.

Ultimately, enhanced substrates to offset the impact of hypomorphic mutations on enzyme activity will be used either as a therapeutic alone or in combination with other agents. Alternative use involves targeted neutraprevention for healthy individuals with circulating hematopoietic cells harboring TET2 mutations and shown to be at risk for developing myeloid neoplasia. Enhanced analogues of α-KG could be used directly in TET2 and UTX mutant cases, but also in those LDH1/2 mutations to displace oncogenic metabolite 2OG and thereby counterbalance the inhibitory effects of onco-metabolites on dioxygenases.

Oncogenic acquired mutations are common cancer. Some of the affected genes encode for proteins with enzymatic activity. Such mutations are commonly hypomorphic and lead to decreased activity of the affected enzyme and inherent downstream consequences. While previous therapeutic strategies targeting oncogenic mutations utilized synthetic lethality or inhibitors of oncogenes, the new strategy proposed herein relies on the principle of up-modulation of the decreased activity of an enzymatic tumor suppressor gene product by compounds agonistic with the natural substrates participating in the reactions catalyzed by the enzymes. By such means the activity of remaining allele can be up-regulated to offset the negative effects of mutations. As described herein, we target two important enzyme-encoding tumor suppressor genes, including demethylases (dioxygenases); and thus propose new agents will be derived from the natural substrates of these enzymes α-KG.

BRIEF DESCRIPTION OF THE FIGURES

FIGS. 1A-1K provide graphs showing the scientific rationale for a TET-modulator. A. TET2 and IDH1/2 mutations are mutually exclusive. IDH1/2MT in patients with TET2MT within a CCF cohort of 1,809 MDS patients and TCGA & BEAT AML cohorts of 808 AML patients. Distribution of TET2 and IDH1/2 mutations was analyzed (Fisher's exact test). In a cohort of 1298 TET2MT cases, TET2MT are found in only 3.0% IDH1/2MT. B. Tet On system for inducible IDH1 expression. TRE3G, Tetracycline-responsive TRE3G promoter; pA, poly A tail; EF1, EF1 promoter; rtTA, reverse tetracycline-controlled transactivator. Cells were treated or not treated with 1 ug/ml Doxycycline (Dox) for 3 days. Anti Flag antibody was used in western blot for the detection of SigM5 (TET2$^{-/-}$) IDH1, IDH1_R132H, and IDH1_R132C, which are tagged with 3×Flag at their N-termini. Three independent clones from each cell line were used. Standard (STD) proteins were harvested from the pool of SigM5 (TET2–/–) IDH1 clones. Same amount of STD proteins were loaded in each SDS-PAGE gel serving as negative and positive controls. C. Production of 2HG measured by LC-MS/MS. Cells was treated with or without 1 ug/ml Doxycycline (Dox) for 3 days before harvesting. D. Dot blot analysis of 5hmC and 5mC in IDH1 inducible SigM5 (TET2–/–) cell line. E. Quantification of 5hmC/5mC of D, n=3. F. 0.1 million/ml of cells were seeded and were treated or not treated with 1 ug/ml Doxycycline (Dox). Cells were counted and passed into a fresh culture media with or without Dox every three days. Three independent clones from each of SigM5 IDH1, IDH1_R132H, and IDH1_R132C were used. G. LD50 of cell permeable 2HG in Molm13. H. Western blot showing generated K562 TET2$^{-/-}$ cell. I. Dot blot analysis of 5hmC and 5mC in K562 TET2$^{-/-}$ cell. J. Quantification of 5hmC/5mC of I, n=3. K. Cell growth curve of K562 TET2$^{+/+}$ and K562 TET2$^{-/-}$ with inducible IDH1_R132C.

FIGS. 2A-2K provide graphs and images showing the lead optimization and efficacy enhancement of TETi. A-B. Consensus binding site for known pseudo substrate NOG (A) and TETi (B). C. 2D structure of α-KG, 2HG and TETi76 salt. D. Coomassie brilliant blue staining of TET2 protein. TET2 was firstly purified by GST tag. Then GST tag was removed by TEV enzyme. E. Dot blot analysis of 5hmC and 5mC for in vitro TET2 enzymatic reaction experiments with TETi76 salt. F. Quantification of 5hmC/5mC of E. G. 2D-structures of TETi. H. survival, as measured by methylene blue exclusion assay after 72 h on a Vi-Cell coulter counter (Beckmann Inc). I. IC$_{50}$ values of different TETi. Data is representative of 3 independent experiments. J. Cells were treated with increasing concentration of indicated TETi and the ratio of 5hmC/5mC was measured and plotted in K.

FIGS. 3A-3G provide graphs showing the In-vitro efficacy of TETi in the elimination of TET2MTcells. A. Leukemia cell lines express different level of TET2. B. Ratio of TET2 expression vs. Lamin C. The dose response curves of cell survival with different concentration of TETi76 D. LD50 plotted against the relative expression of TET2 and C. E. Colony forming abilities of K562 TET2$^{+/+}$ and TET2$^{-/-}$ cells in the presence and absence of TETi76. Data is representative of 3 independent experiment performed separately. F. Colony forming abilities of two independent normal bone marrow cells (NBM) and SIGM5 cells in MethoCult in the presence and absence of TETi76. Data is the summary of three independent experiments performed separately. G. Bone marrow from Tet2$^{+/+}$, Tet2$^{+/-}$ and Tet2$^{-/-}$ mice were harvested and cultured in MethoCult in the presence or absence of TETi76.

FIGS. 4A-4E provide graphs and images showing the In-vivo efficacy of TETi in the elimination of cells with TET2$^{MT}$. A. Diagram shows the mixing experiment of Tet$^{wt}$ and Tet$^{mt}$ assay. Tet$^{mt}$ bone marrow cells were mixed in the ratio of 1:2 with tet2$^{+/+}$ bone marrow cells isolated from Pep (CD45.1). The mixed bone marrow cells were treated either with DMSO or with TETi76 in MethoCult™. Cells were isolated and ratio of CD45.1 (Pep, tet2$^{+/+}$) and CD45.2 (tet2mt) was determined by flow using antibodies against CD45.1 and CD45.2. B. Tet2$^{+/-}$ bone marrow cells were mixed in the ratio of 1:2 with Tet2$^{+/+}$ in MethoCult with the treatment of DMSO or TETi76. Ratio of Tet2$^{+/-}$ vs Tet2$^{+/+}$ was measured by flow. C. Tet2$^{+/-}$ bone marrow cells were mixed in the ratio of 1:2 with Tet2$^{+/+}$ in MethoCult with the treatment of DMSO or TETi76. Cells were cultured and replated with or without 20 μM TETi76. Ratio of Tet2$^{+/-}$ vs Tet2$^{+/+}$ was measured by flow. D. Diagram shows the TETi treatment experiment in vivo. E. TETi76 prevents clonal expansion Tet2MT cells in vivo. Each of 6 recipient mice (CD45.1) received a mixture donor mice bone marrows (5% Tet2$^{-/-}$, CD45.2; and 95% Tet2$^{+/+}$) after irradiation and transplant. TETi76 was administered s.c., into 3 mice. Other 3 mice received 10% cyclodextrin were server as controls. CD45.1+ vs. CD45.2+ was serially assessed.

FIGS. 6A and 6B provide sequences and a reaction scheme A. The catalytic residues among TET proteins are highly conserved. Residues H1382, S1898 and H1801 interacting with TETi are identically positioned in all TETs. B. Synthetic scheme for α-KG scaffold-based TET inhibitors. The starting material will be purchased the reaction conditions are annotated for each reaction.

DETAILED DESCRIPTION OF THE INVENTION

Figure 5A:
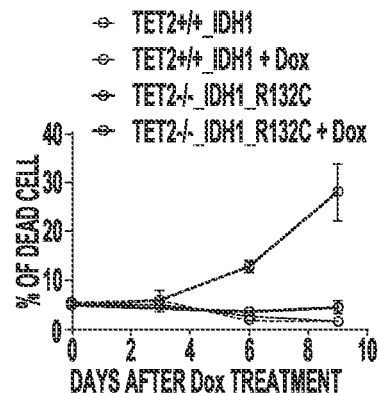
FIGS. 5A and 5B provide a graph and schematic representation showing A. Cell viability analysis. B. Effects of TET2MT and mechanistic underpinning of the predictive effects of TET inhibitor as a possible therapeutic for MDS.

The present invention provides a method of treating cancer in a subject that includes administering a therapeutically effective amount of a compound of Formula I:

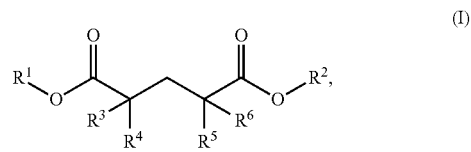
(I)

a compound of Formula II:

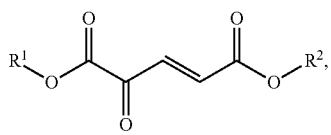

or a compound of Formula III:

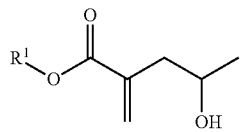

to a subject in need thereof. The present invention also provides method of treating or preventing cancer in a subject that includes the step of analyzing a biological sample to determine if cells of the biological sample exhibit a TET2 mutation.

Definitions

The terminology as set forth herein is for description of the embodiments only and should not be construed as limiting of the invention as a whole. Unless otherwise specified, "a," "an," "the," and "at least one" are used interchangeably. Furthermore, as used in the description of the invention and the appended claims, the singular forms "a", "an", and "the" are inclusive of their plural forms, unless contraindicated by the context surrounding such.

The terms "comprising" and variations thereof do not have a limiting meaning where these terms appear in the description and claims.

As used herein, the term "organic group" is used for the purpose of this invention to mean a hydrocarbon group that is classified as an aliphatic group, cyclic group, or combination of aliphatic and cyclic groups (e.g., alkaryl and aralkyl groups). In the context of the present invention, suitable organic groups for TET2 modulators are those that do not interfere with the compounds anticancer activity. In the context of the present invention, the term "aliphatic group" means a saturated or unsaturated linear or branched hydrocarbon group. This term is used to encompass alkyl, alkenyl, and alkynyl groups, for example.

As used herein, the terms "alkyl", "alkenyl", and the prefix "alk-" are inclusive of straight chain groups and branched chain groups and cyclic groups, e.g., cycloalkyl and cycloalkenyl. Unless otherwise specified, these groups contain from 1 to 20 carbon atoms, with alkenyl groups containing from 2 to 20 carbon atoms. In some embodiments, these groups have a total of at most 10 carbon atoms, at most 8 carbon atoms, at most 6 carbon atoms, or at most 4 carbon atoms. Lower alkyl groups are those including at most 6 carbon atoms. Examples of alkyl groups include haloalkyl groups and hydroxyalkyl groups.

Unless otherwise specified, "alkylene" and "alkenylene" are the divalent forms of the "alkyl" and "alkenyl" groups defined above. The terms, "alkylenyl" and "alkenylenyl" are used when "alkylene" and "alkenylene", respectively, are substituted. For example, an arylalkylenyl group comprises an alkylene moiety to which an aryl group is attached.

The term "haloalkyl" is inclusive of groups that are substituted by one or more halogen atoms, including perfluorinated groups. This is also true of other groups that include the prefix "halo-". Examples of suitable haloalkyl groups are chloromethyl, trifluoromethyl, and the like. A halo moiety can be chlorine, bromine, fluorine, or iodine.

Cycloalkyl groups are cyclic alkyl groups containing 3, 4, 5, 6, 7 or 8 ring carbon atoms like cyclopropyl, cyclobutyl, cyclopentyl, cyclohexyl or cyclooctyl, which can also be substituted and/or contain 1 or 2 double bounds (unsaturated cycloalkyl groups) like, for example, cyclopentenyl or cyclohexenyl can be bonded via any carbon atom.

A heterocyclyl group means a mono- or bicyclic ring system in which one or more carbon atoms can be replaced by one or more heteroatoms such as, for example, 1, 2 or 3 nitrogen atoms, 1 or 2 oxygen atoms, 1 or 2 sulfur atoms or combinations of different hetero atoms. The heterocyclyl residues can be bound at any positions, for example on the 1-position, 2-position, 3-position, 4-position, 5-position, 6-position, 7-position or 8-position.

The term "aryl" as used herein includes carbocyclic aromatic rings or ring systems. Examples of aryl groups include phenyl, naphthyl, biphenyl, anthracenyl, phenanthracenyl, fluorenyl and indenyl. Aryl groups may be substituted or unsubstituted.

Unless otherwise indicated, the term "heteroatom" refers to the atoms O, S, or N.

The term "heteroaryl" includes aromatic rings or ring systems that contain at least one ring heteroatom (e.g., O, S, N). In some embodiments, the term "heteroaryl" includes a ring or ring system that contains 2 to 12 carbon atoms, 1 to 3 rings, 1 to 4 heteroatoms, and O, S, and/or N as the heteroatoms. Suitable heteroaryl groups include furyl, thienyl, pyridyl, quinolinyl, isoquinolinyl, indolyl, isoindolyl, triazolyl, pyrrolyl, tetrazolyl, imidazolyl, pyrazolyl, oxazolyl, thiazolyl, benzofuranyl, benzothiophenyl, carbazolyl, benzoxazolyl, pyrimidinyl, benzimidazolyl, quinoxalinyl, benzothiazolyl, naphthyridinyl, isoxazolyl, isothiazolyl, purinyl, quinazolinyl, pyrazinyl, 1-oxidopyridyl, pyridazinyl, triazinyl, tetrazinyl, oxadiazolyl, thiadiazolyl, and so on.

When a group is present more than once in any formula or scheme described herein, each group (or substituent) is independently selected, whether explicitly stated or not. For example, for the formula —C(O)—NR$_2$ each R group is independently selected. In addition, in some embodiments, a group is identified as being optional. An optional group may be entirely absent in some embodiments of the invention, but present in others.

As a means of simplifying the discussion and the recitation of certain terminology used throughout this application, the terms "group" and "moiety" are used to differentiate between chemical species that allow for substitution or that may be substituted and those that do not so allow for substitution or may not be so substituted. Thus, when the term "group" is used to describe a chemical substituent, the described chemical material includes the unsubstituted group and that group with non-peroxidic O, N, S, Si, or F atoms, for example, in the chain as well as carbonyl groups or other conventional substituents. Where the term "moiety" is used to describe a chemical compound or substituent, only an unsubstituted chemical material is intended to be included. For example, the phrase "alkyl group" is intended to include not only pure open chain saturated hydrocarbon alkyl substituents, such as methyl, ethyl, propyl, tert-butyl, and the like, but also alkyl substituents bearing further substituents known in the art, such as hydroxy, alkoxy, alkylsulfonyl, halogen atoms, cyano, nitro, amino, carboxyl, etc. Thus, "alkyl group" includes ether groups, haloalkyls, nitroalkyls, carboxyalkyls, hydroxyalkyls, sulfoalkyls, etc. On the other hand, the phrase "alkyl moiety" is limited to the inclusion of only pure open chain saturated hydrocarbon alkyl substituents, such as methyl, ethyl, propyl, tert-butyl, and the like.

Asymmetric centers exist in the compounds of the present invention. These centers are designated by the symbols "R" or "S," depending on the configuration of substituents around the chiral carbon atom. It should be understood that the invention encompasses all stereochemical isomeric forms, including diastereomeric, enantiomeric, and epimeric forms, as well as d-isomers and l-isomers, and mixtures thereof. Individual stereoisomers of compounds can be prepared synthetically from commercially available starting materials which contain chiral centers or by preparation of mixtures of enantiomeric products followed by separation such as conversion to a mixture of diastereomers followed by separation or recrystallization, chromatographic techniques, direct separation of enantiomers on chiral chromatographic columns, or any other appropriate method known in the art. Starting compounds of particular stereochemistry are either commercially available or can be made and resolved by techniques known in the art. Additionally, the compounds of the present invention may exist as geometric isomers. The present invention includes all cis, trans, syn, anti, entgegen (E), and zusammen (Z) isomers as well as the appropriate mixtures thereof. Additionally, compounds may exist as tautomers; all tautomeric isomers are provided by this invention. Additionally, the compounds of the present invention can exist in unsolvated as well as solvated forms with pharmaceutically acceptable solvents such as water, ethanol, and the like. In general, the solvated forms are considered equivalent to the unsolvated forms for the purposes of the present invention.

"Treat", "treating", and "treatment", etc., as used herein, refer to any action providing a benefit to a patient at risk for or afflicted with a disease, including improvement in the condition through lessening or suppression of at least one symptom, delay in progression of the disease, prevention or delay in the onset of the disease, etc. Treatment also includes partial or total destruction or differentiation of the undesirable proliferating cells with minimal effects on normal cells. In accordance with the present invention, desired mechanisms of treatment at the cellular level include stimulation of differentiation in cancer and pre-cancer cells.

As used herein, the term "prevention" includes either preventing the onset of a clinically evident unwanted cell proliferation altogether or preventing the onset of a preclinically evident stage of unwanted rapid cell proliferation in individuals at risk. Also intended to be encompassed by this definition is the prevention of metastasis of malignant cells or to arrest or reverse the progression of malignant cells. This includes prophylactic treatment of those having an enhanced risk of developing precancers and cancers. An elevated risk represents an above-average risk that a subject will develop cancer, which can be determined, for example, through family history or the detection of genes causing a predisposition to developing cancer.

"Pharmaceutically acceptable" as used herein means that the compound or composition is suitable for administration to a subject to achieve the treatments described herein, without unduly deleterious side effects in light of the severity of the disease and necessity of the treatment.

The terms "therapeutically effective" and "pharmacologically effective" are intended to qualify the amount of each agent which will achieve the goal of decreasing disease severity while avoiding adverse side effects such as those typically associated with alternative therapies. The therapeutically effective amount may be administered in one or more doses.

An effective amount, on the other hand, is an amount sufficient to provide a significant chemical effect, such as the inhibition of cancer growth by a detectable amount.

A "subject," as used herein, can be any animal, and may also be referred to as the patient. Preferably the subject is a vertebrate animal, and more preferably the subject is a mammal, such as a domesticated farm animal (e.g., cow, horse, pig) or pet (e.g., dog, cat). In some embodiments, the subject is a human.

TET2 Modulators

In one aspect, the present invention provides α-KG analogs that can be used to modulate TET2 activity. Modulation includes either activating or inhibiting the activity of TET2. Examples of α-KG analogs include compounds of Formula I:

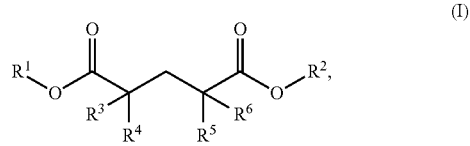

wherein $R^1$ and $R^2$ are independently selected from H, $CH_3$, $CH_2CH_3$, and $C_1$-$C_6$ alkyl, $R^3$ and $R^4$ are H and —$CH_3$, or $R^3$ and $R^4$ are combined to form =$CH_2$ or a cyclopropyl group; and $R^5$ and $R^6$ are independently selected from H, halogen, —OH, —$CF_3$, $C_1$-$C_6$ alkyl, or $R^5$ and $R^6$ are combined to form =O; and compounds of Formula II:

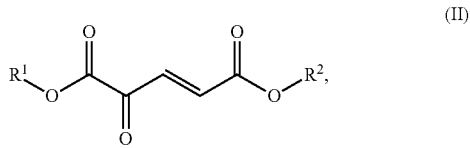

wherein $R^1$ and $R^2$ are independently selected from H, $CH_3$, $CH_2CH_3$, and $C_1$-$C_6$ alkyl; and compounds of Formula III:

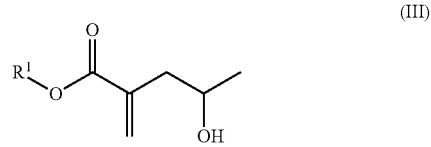

wherein $R^1$ is selected from H, $CH_3$, $CH_2CH_3$, and $C_1$-$C_6$ alkyl; and pharmaceutically acceptable salt thereof.

In some embodiments, the compound is a compound according to formula I, while in other embodiments the compound is a compound according to formula II or a compound according to formula III. In further embodiments, the compound is one in which $R^3$ and $R^4$ are combined to form =$CH_2$.

In further embodiments, the compound is a compound selected from the group consisting of TETi76, TETi143, SynMed3a, TETi123, TETi152, TETi211, TETi31, TETi125, TETi186, TETi220, TETi37, TETi131, and TETi187, the structures of which are shown below:

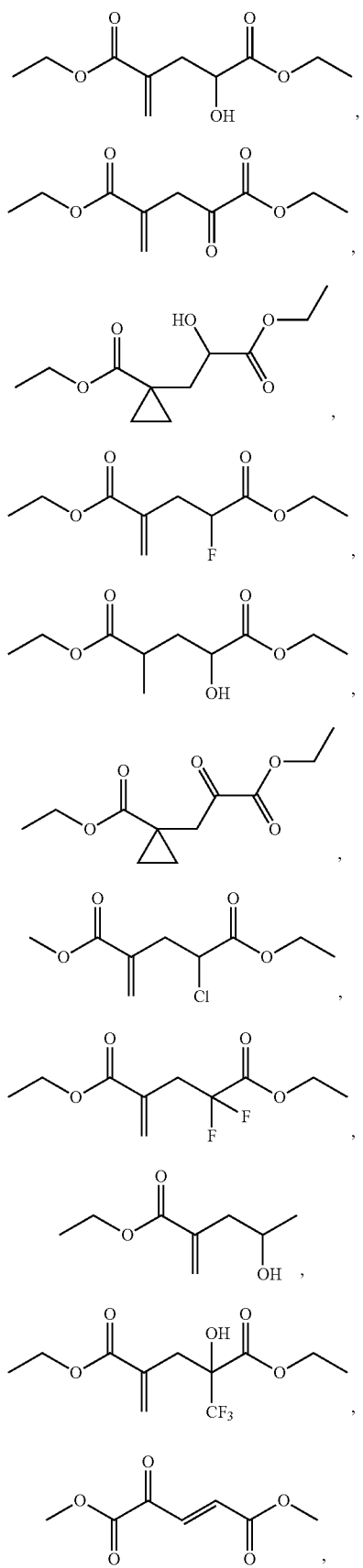

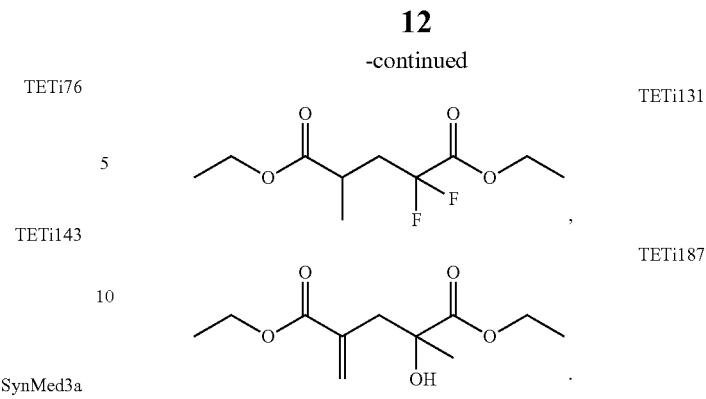

In some embodiments, the TET2 modulator is a compound selected from TETi76, TETi187, or TETi220. In further embodiments, the compound is either the R or S isomer of TETi76.

In some embodiments, suitable TET2 modulators can be identified through analysis of their interaction with the TET enzyme. For example, the potential TET2 modulators can be evaluated through their interaction with amino acid sequences present in the TET enzyme. Examples of such sequences are shown in FIG. 6A, which shows that the catalytic residues among TET proteins are highly conserved. Residues H1382, S1898 and H1801 interacting with TETi are identically positioned in all TETs. The TETs shown are amino acids from human TET1 (SEQ ID NO: 1), amino acids from human TET2 (SEQ ID NO: 2), and amino acids from human TET3 (SEQ ID NO: 3).

Treatment of Cancer Using TET2 Modulators

In another aspect, the present invention provides methods for treating cancer in a subject in need thereof by administering a therapeutically effective amount of a compound (i.e., an α-KG analog) of Formula I:

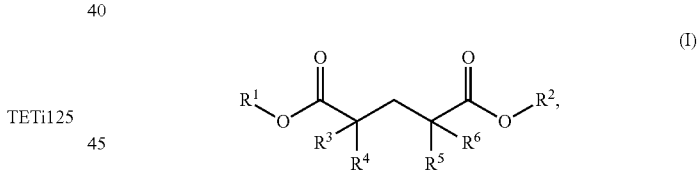

wherein $R^1$ and $R^2$ are independently selected from H, $CH_3$, $CH_2CH_3$, and $C_1$-$C_6$ alkyl, $R^3$ and $R^4$ are H and —$CH_3$, or $R^3$ and $R^4$ are combined to form =$CH_2$ or a cyclopropyl group; and $R^5$ and $R^6$ are independently selected from H, halogen, —OH, —$CF_3$, $C_1$-$C_6$ alkyl, or $R^5$ and $R^6$ are combined to form =O; and compounds of Formula II:

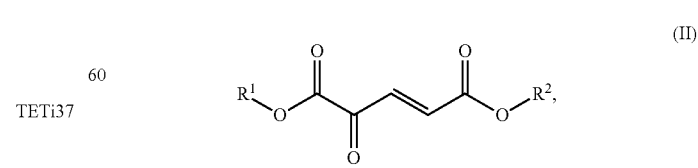

wherein $R^1$ and $R^2$ are independently selected from H, $CH_3$, $CH_2CH_3$, and $C_1$-$C_6$ alkyl; and compounds of Formula III:

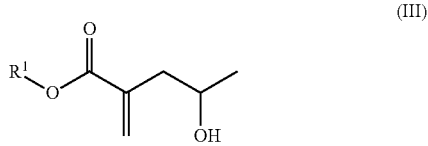

(III)

wherein $R^1$ is selected from H, $CH_3$, $CH_2CH_3$, and $C_1$-$C_6$ alkyl; and pharmaceutically acceptable salt thereof.

In some embodiments, the compound is a compound according to formula I. In other embodiments, the compound is a compound according to formula II or formula III. In further embodiments, the compound is one in which $R^3$ and $R^4$ are combined to form =$CH_2$. In further embodiments, the compound is a compound selected from the group consisting of TETi76, TETi143, SynMed3a, TETi123, TETi152, TETi211, TETi31, TETi125, TETi186, TETi220, TETi37, TETi131, and TETi187. In some embodiments, the TET2 modulator is a compound selected from TETi76, TETi187, or TETi220. In further embodiments, the compound is either the R or S isomer of TETi76.

The method of using TET2 modulators also includes the use of pharmaceutically acceptable salts of the compounds encompassed by Formulas I, II, and III. The method also encompasses embodiments including the use of any of the subsets of TET2 inhibitor described herein. In some embodiments, the TET2 modulator is administered together with a pharmaceutically acceptable carrier.

Cancer is a disease of abnormal and excessive cell proliferation. Cancer is generally initiated by an environmental insult or error in replication that allows a small fraction of cells to escape the normal controls on proliferation and increase their number. The damage or error generally affects the DNA encoding cell cycle checkpoint controls, or related aspects of cell growth control such as tumor suppressor genes. As this fraction of cells proliferates, additional genetic variants may be generated, and if they provide growth advantages, will be selected in an evolutionary fashion. Cells that have developed growth advantages but have not yet become fully cancerous are referred to as precancerous cells. Cancer results in an increased number of cancer cells in a subject. These cells may form an abnormal mass of cells called a tumor, the cells of which are referred to as tumor cells. The overall amount of tumor cells in the body of a subject is referred to as the tumor load. Tumors can be either benign or malignant. A benign tumor contains cells that are proliferating but remain at a specific site and are often encapsulated. The cells of a malignant tumor, on the other hand, can invade and destroy nearby tissue and spread to other parts of the body through a process referred to as metastasis.

Cancer is generally named based on its tissue of origin. There are several main types of cancer. Carcinoma is cancer that begins in the skin or in tissues that line or cover internal organs. Sarcoma is cancer that begins in bone, cartilage, fat, muscle, blood vessels, or other connective or supportive tissue. Leukemia is cancer that starts in blood-forming tissue such as the bone marrow, and causes large numbers of abnormal blood cells to be produced and enter the bloodstream. Lymphoma and multiple myeloma are cancers that begin in the cells of the immune system. Examples of types of cancer that can be treated using the compounds of the present invention include cancer is selected from the group consisting of bladder cancer, prostate cancer, liver cancer, breast cancer, colon cancer, and leukemia. In some embodiments, the cancer being treated is a cancer having a TET2 mutation. In further embodiments, the cancer is selected from myelodysplastic syndrome, myeloproliferative neoplasm, and acute myeloid leukemia.

The TET2 modulators of the invention can be used for both prophylactic and therapeutic treatment. When used for cancer treatment, the TET2 modulators can be referred to as anticancer, or antitumor agents. The TET2 modulators can, for example, be administered prophylactically to a mammal prior to the development of cancer. Prophylactic administration, also referred to as prevention, is effective to decrease the likelihood that cancer will develop in the subject. For prophylactic treatment, the subject is any human or animal subject, and preferably is a human subject who is at risk of acquiring a disorder characterized by unwanted, rapid cell proliferation, such as cancer. The subject may be at risk due to exposure to carcinogenic agents, being genetically predisposed to disorders characterized by unwanted, rapid cell proliferation, and so on.

Alternatively, TET2 modulators of the invention can, for example, be administered therapeutically to a subject that already has cancer. For purposes of treatment, a subject at risk includes any human or animal subject who has a disorder characterized by unwanted, rapid cell proliferation. Such disorders include, but are not limited to cancers and precancers. In one embodiment of therapeutic administration, administration of the TET2 modulators is effective to eliminate the cancer; in another embodiment, administration of the TET2 modulators is effective to decrease the symptoms or spread of the cancer.

The effectiveness of cancer treatment may be measured by evaluating a reduction in tumor load or decrease in tumor growth in a subject in response to the administration of the TET2 modulators. The reduction in tumor load may be represent a direct decrease in mass, or it may be measured in terms of tumor growth delay, which is calculated by subtracting the average time for control tumors to grow over to a certain volume from the time required for treated tumors to grow to the same volume.

Candidate agents may be tested in animal models. Typically, the animal model is one for the study of cancer. The study of various cancers in animal models (for instance, mice) is a commonly accepted practice for the study of human cancers. For instance, the nude mouse model, where human tumor cells are injected into the animal, is commonly accepted as a general model useful for the study of a wide variety of cancers (see, for instance, Polin et al., Investig. New Drugs, 15:99-108 (1997)). Results are typically compared between control animals treated with candidate agents and the control littermates that did not receive treatment. Transgenic animal models are also available and are commonly accepted as models for human disease (see, for instance, Greenberg et al., Proc. Natl. Acad. Sci. USA, 92:3439-3443 (1995)). Candidate agents can be used in these animal models to determine if a candidate agent decreases one or more of the symptoms associated with the cancer, including, for instance, cancer metastasis, cancer cell motility, cancer cell invasiveness, or combinations thereof. In some embodiments, candidate anticancer agents can be detected using an in vitro assay system, such as the luciferase-based reporter assay for CEBPE promoter activity.

Methods of cancer treatment using the compounds described herein can further include the step of ablating the cancer. Ablating the cancer can be accomplished using a method selected from the group consisting of cryoablation, thermal ablation, radiotherapy, chemotherapy, radiofrequency ablation, electroporation, alcohol ablation, high intensity focused ultrasound, photodynamic therapy, administration of monoclonal antibodies, and administration of immunotoxins.

Treatment or Prevention with TET2 Mutation Detection

In another aspect, the present invention provides a method of treating or preventing cancer in a subject that includes the step of determining if the subject exhibits a TET2 mutation. The method of preventing cancer includes providing a biological sample from the subject, analyzing the biological sample to determine if cells of the biological sample exhibit a TET2 mutation, and administering an effective amount of a TET2 activator to the subject if a TET2 mutation is present. Because TET2 mutations are relatively common in older subjects, and because TET2 mutations have been shown to be associated with neoplasm development, detection of the TET2 mutation provides a useful means to provide appropriate prophylactic treatment only to subjects in need of such treatment. In some embodiments, the method is used to treat or prevent myelodysplastic syndrome, myeloproliferative neoplasm, or acute myeloid leukemia.

The TET2 activator used in a method of preventing cancer can be compounds of Formula I:

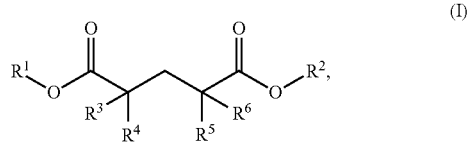

(I)

wherein $R^1$ and $R^2$ are independently selected from H, $CH_3$, $CH_2CH_3$, and $C_1$-$C_6$ alkyl, $R^3$ and $R^4$ are H and —$CH_3$, or $R^3$ and $R^4$ are combined to form =$CH_2$ or a cyclopropyl group; and $R^5$ and $R^6$ are independently selected from H, halogen, —OH, —$CF_3$, $C_1$-$C_6$ alkyl, or $R^5$ and $R^6$ are combined to form =O; and compounds of Formula II:

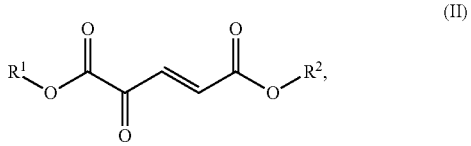

(II)

wherein $R^1$ and $R^2$ are independently selected from H, $CH_3$, $CH_2CH_3$, and $C_1$-$C_6$ alkyl; and compounds of Formula III:

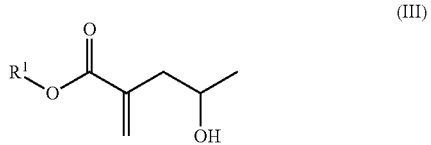

(III)

wherein $R^1$ is selected from H, $CH_3$, $CH_2CH_3$, and $C_1$-$C_6$ alkyl; and pharmaceutically acceptable salt thereof.

In some embodiments, the compound is one in which $R^3$ and $R^4$ are combined to form =$CH_2$. In further embodiments, the compound is a compound selected from the group consisting of TETi76, TETi143, SynMed3a, TETi123, TETi152, TETi211, TETi31, TETi125, TETi186, TETi220, TETi37, TETi131, and TETi187. In some embodiments, the TET2 modulator is a compound selected from TETi76, TETi187, or TETi220. In further embodiments, the compound is either the R or S isomer of TETi76.

Biological samples include, but are not necessarily limited to bodily fluids such as saliva, urine and blood-related samples (e.g., whole blood, serum, plasma, and other blood-derived samples), cerebral spinal fluid, bronchoalveolar lavage, and the like. In some embodiments, the biological sample is a skin sample. Biological samples can be obtained by any known means including needle stick, needle biopsy, swab, and the like.

A biological sample may be fresh or stored (e.g. blood or blood fraction stored in a blood bank). Samples can be stored for varying amounts of time, such as being stored for an hour, a day, a week, a month, or more than a month. The biological sample may be a bodily fluid expressly obtained for the assays of this invention or a bodily fluid obtained for another purpose which can be sub-sampled in order to carry out the method.

Administration and Formulation

In some embodiments, the compound of formula I or formula II is administered together with a pharmaceutically acceptable carrier. The invention provides pharmaceutical compositions that include TET2 modulators according to formula I or formula II as an active ingredient, and a pharmaceutically acceptable liquid or solid carrier or carriers, in combination with the active ingredient. Any of the compounds described above as being suitable for the treatment of cancer can be included in pharmaceutical compositions of the invention.

The TET2 modulators can be administered as pharmaceutically acceptable salts. Pharmaceutically acceptable salt refers to the relatively non-toxic, inorganic and organic acid addition salts of the TET2 modulators. These salts can be prepared in situ during the final isolation and purification of the TET2 modulators, or by separately reacting a purified TET2 inhibitor with a suitable counterion, depending on the nature of the compound, and isolating the salt thus formed. Representative counterions include the chloride, bromide, nitrate, ammonium, sulfate, tosylate, phosphate, tartrate, ethylenediamine, and maleate salts, and the like. See for example Haynes et al., J. Pharm. Sci., 94, p. 2111-2120 (2005).

The pharmaceutical compositions includes one or more TET2 modulators together with one or more of a variety of physiological acceptable carriers for delivery to a patient, including a variety of diluents or excipients known to those of ordinary skill in the art. For example, for parenteral administration, isotonic saline is preferred. For topical administration, a cream, including a carrier such as dimethylsulfoxide (DMSO), or other agents typically found in topical creams that do not block or inhibit activity of the peptide, can be used. Other suitable carriers include, but are not limited to, albumin, alcohol, phosphate buffered saline, and other balanced salt solutions.

The formulations may be conveniently presented in unit dosage form and may be prepared by any of the methods well known in the art of pharmacy. Preferably, such methods include the step of bringing the active agent into association with a carrier that constitutes one or more accessory ingredients. In general, the formulations are prepared by uniformly and intimately bringing the active agent into association with a liquid carrier, a finely divided solid carrier, or both, and then, if necessary, shaping the product into the desired formulations. The methods of the invention include administering to a subject, preferably a mammal, and more preferably a human, the composition of the invention in an amount effective to produce the desired effect. The TET2 modulators can be administered as a single dose or in multiple doses. Useful dosages of the active agents can be determined by comparing their in vitro activity and the in vivo activity in animal models. Methods for extrapolation of effective dosages in mice, and other animals, to humans are known in the art; for example, see U.S. Pat. No. 4,938,949.

The agents of the present invention are preferably formulated in pharmaceutical compositions and then, in accordance with the methods of the invention, administered to a subject, such as a human patient, in a variety of forms adapted to the chosen route of administration. The formulations include, but are not limited to, those suitable for oral, rectal, vaginal, topical, nasal, ophthalmic, or parental (including subcutaneous, intramuscular, intraperitoneal, intratumoral, and intravenous) administration.

Formulations of the present invention suitable for oral administration may be presented as discrete units such as tablets, troches, capsules, lozenges, wafers, or cachets, each containing a predetermined amount of the active agent as a powder or granules, as liposomes containing the TET2 modulators, or as a solution or suspension in an aqueous liquor or non-aqueous liquid such as a syrup, an elixir, an emulsion, or a draught. Such compositions and preparations typically contain at least about 0.1 wt-% of the active agent. The amount of TET2 inhibitor (i.e., active agent) is such that the dosage level will be effective to produce the desired result in the subject.

Nasal spray formulations include purified aqueous solutions of the active agent with preservative agents and isotonic agents. Such formulations are preferably adjusted to a pH and isotonic state compatible with the nasal mucous membranes. Formulations for rectal or vaginal administration may be presented as a suppository with a suitable carrier such as cocoa butter, or hydrogenated fats or hydrogenated fatty carboxylic acids. Ophthalmic formulations are prepared by a similar method to the nasal spray, except that the pH and isotonic factors are preferably adjusted to match that of the eye. Topical formulations include the active agent dissolved or suspended in one or more media such as mineral oil, petroleum, polyhydroxy alcohols, or other bases used for topical pharmaceutical formulations.

The tablets, troches, pills, capsules, and the like may also contain one or more of the following: a binder such as gum tragacanth, acacia, corn starch or gelatin; an excipient such as dicalcium phosphate; a disintegrating agent such as corn starch, potato starch, alginic acid, and the like; a lubricant such as magnesium stearate; a sweetening agent such as sucrose, fructose, lactose, or aspartame; and a natural or artificial flavoring agent. When the unit dosage form is a capsule, it may further contain a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac, sugar, and the like. A syrup or elixir may contain one or more of a sweetening agent, a preservative such as methyl- or propylparaben, an agent to retard crystallization of the sugar, an agent to increase the solubility of any other ingredient, such as a polyhydric alcohol, for example glycerol or sorbitol, a dye, and flavoring agent. The material used in preparing any unit dosage form is substantially nontoxic in the amounts employed. The active agent may be incorporated into sustained-release preparations and devices.

Preparation of the Compounds

Compounds of the invention may be synthesized by synthetic routes that include processes similar to those well known in the chemical arts, particularly in light of the description contained herein. The starting materials are generally available from commercial sources such as Aldrich Chemicals (Milwaukee, Wisconsin, USA) or are readily prepared using methods well known to those skilled in the art (e.g., prepared by methods generally described in Louis F. Fieser and Mary Fieser, *Reagents for Organic Synthesis*, v. 1-19, Wiley, New York, (1967-1999 ed.); Alan R. Katritsky, Otto Meth-Cohn, Charles W. Rees, *Comprehensive Organic Functional Group Transformations*, v 1-6, Pergamon Press, Oxford, England, (1995); Barry M. Trost and Ian Fleming, *Comprehensive Organic Synthesis*, v. 1-8, Pergamon Press, Oxford, England, (1991); or *Beilsteins Handbuch der organischen Chemie,* 4, Aufl. Ed. Springer-Verlag, Berlin, Germany, including supplements (also available via the Beilstein online database)).

Those skilled in the art will appreciate that other synthetic routes may be used to synthesize the compounds of the invention. Although specific starting materials and reagents are depicted in the reaction schemes and discussed below, other starting materials and reagents can be easily substituted to provide a variety of derivatives and/or reaction conditions. In addition, many of the compounds prepared by the methods described below can be further modified in light of this disclosure using conventional methods well known to those skilled in the art.

The present invention is illustrated by the following examples. It is to be understood that the particular examples, materials, amounts, and procedures are to be interpreted broadly in accordance with the scope and spirit of the invention as set forth herein.

EXAMPLES

Example 1: Synthetic Lethality of α-Ketoglutarate Antagonists in TET2 Mutant Leukemias TET2 is one of the most commonly mutated genes in MDS or related diseases and frequent in clonal hematopoiesis of indeterminate potential (CHIP). Mutual exclusivity of 2HG-producing IDH1/2$^{MT}$ and TET2 mutations (TET2$^{MT}$) and dependence of TET2-deficient cells on residual DNA dioxygenase-activity from low-expressed TET1 and TET3, to the hypothesis that inhibition of remaining TET-activity may lead to synthetic lethality to the TET2$^{MT}$ clones and will have great therapeutic utility. We observed that ectopic expression of IDH1/2$^{MT}$ that significantly increased the 2HG production, is selectively lethal to TET2$^{MT}$ cells. We also observed that structurally guided small molecule analogues can selectively eliminate TET2$^{MT}$ cells with a clinically-applicable therapeutic index. This selectivity for TET2$^{MT}$ cells is likely due to inhibition of the residual TET-activity. While IDH1/2$^{MT}$ permanently produce the weak TET2-inhibiting oncometabolite, the TET-inhibition as a therapeutic intervention can be safely applied and discontinued upon elimination of the vulnerable TET2-deficient cells. We have asserted that indeed TET inhibitors (TETi) do have selective activity in invitro and in vivo models of TET2$^{MT}$. Here, we propose to develop a novel targeted therapeutic approach for TET2$^{MT}$ MDS involving highly specific TETi, a new class of DNA dioxygenase-inhibiting agent. Our objectives are: i) to generate and test TETi in cell-free, ex vivo and in in vivo pre-clinical models in both preventative and therapeutic modes; ii) to provide a preclinical proof of concept for development of drugs for rational application in TET2$^{MT}$ myeloid neoplasia. Thus, we have formulated the following Specific Objectives (SAs).

SA1. Perform structure-guided refinement of TETi's. A focused small molecule library modeled on the lead TETi that preferentially bind and inhibit TET DNA dioxygenase will be designed, synthesized and will be tested in TET-activity assays using LCMS and DNA with hmC as a readout. While the initial design will be modeled on TET2, the specificity will be validated against TET1, TET3 and other αKG utilizing dioxygenases. Cell-permeable esterified forms will be synthesized for experiments in SA2/3.

SA2. Establish the effects of TETi compounds in vitro human and murine models. Selected TETi (cell-permeable esters) will be tested for their efficacy in specific genetic context. Experiments will be performed with natural TET2$^{MT}$ cell lines (SIGM5, OCI-AML5, HEL and MEG01), genetically manipulated cell lines (K562 and MOLM13) and therapeutic index will be determined using normal CD34+ cells, patient-derived (biallelic or heterozygous TET2$^{MT}$) cells and HSPC derived from tet2$^{+/-}$ and tet2$^{-/-}$ mice. Primary readouts will include hmC levels, proliferation, and gene expression.

SA3. Characterize TETi 'leads' in preventative and therapeutic as well as tolerability in pre-clinical murine models. We will evaluate TETi's abilities to delay/prevent MDS/MPN evolution and to retard progression of transplanted MPN/MDS cells including those arising spontaneously in tet2/− mice and those arising sooner in crosses with more aggressive phenotype, e.g., tet2$^{+/-}$-flt3, NUP98/HOX9A/tet2$^{+/-}$. Thus interventions will be explored in both preventative and therapeutic models. Readouts will include: survival, progression, morphology and hmC levels in DNA of harvested cells. TETi will also be tested in a "preclinical trial" of primary human PDX with defined molecular feature to test TETi selectivity.

Scientific and Clinical Significance & Preliminary results Clinical spectrum of TET2$^{MT}$. Somatic TET2$^{MT}$ are common genetic defects in hematologic neoplasms, including MDS, MPN and AML. TET2$^{MT}$ are ancestral in ~50% of cases and their incidence increases with age. Over 70% of MDS patients 80 y or older have TET2$^{MT}$. Consistent with these findings, TET2$^{MT}$ CHIP is also related to aging. Jaiswal, S. et al. The New England journal of medicine 371, 2488-2498, (2014). The frequency of TET2$^{MT}$ in healthy elderly increases with aging. When analyzing our large cohort of patients (>5000) we identified 1205 cases with 1781 TET2$^{MT}$ (FIG. 1A). Our studies showed distribution and configuration of TET2$^{MT}$ among disease sub-entities including hemi-, homozygous and biallelic lesions (up to 50% in CMML) and observed that 47% of TET2$^{MT}$ were frameshifts, 20% missense mutations (88% active site). Configuration of biallelic mutations included double frameshifts in 110/557 (~11%), mostly loss of function mutations.

Clinical hierarchy of TET2$^{MT}$:TET2$^{MT}$ had the highest VAF and thus ancestral in 65% of the patients. Our recent study (1800 pts with targeted NGS) indicate that ancestral TET2 hits are followed by 2nd TET2 hit or/and sub-clonal SRSF2/ZRSR2 and ASXL1 hits. One important conclusion of our clinical studies is that MDS often begins with an ancestral TET2$^{MT}$ prior to MDS onset (often originating in CHIP1. While one can calculate that only a minority of TET2$^{MT}$ CHIP cases end up with MDS, the impact of TET2$^{MT}$ and the growing etiologic fraction of TET2$^{MT}$ with age is tremendous. High incidence of TET2$^{MT}$ in myeloid neoplasia with a strong age-relationship suggests that TET2 is a key player in MDS pathogenesis. Ancestral nature of TET2$^{MT}$ implies that targeting this mutation could disrupt the clone at its foundation and further indicates that it is a rational target for preventive strategies, since the clone in such stages is likely to be dependent on TET2 loss.

Clinical clues to therapeutic approaches. Bialleic hits are present in 20-30% of mutant cases, but progressive inactivation of TET2 locus is not associated with increased risk of progression or negative impact on survival but rather contribute to increased monocytic skewing and indicates that further inhibition of dioxygenases function does not accelerate progression. Beer, P. A. et al., Blood 115, 2891-2900 (2010). TET2 has 2 homologs, TET1 and TET3, but their expressions are very low in HSC. Previously, conditional knockdown of tet1 in the tet2-deficient background (tet2$^{-/-}$tet$^{-/-}$) was shown to induce myeloid or lymphoid leukemias in genetically manipulated mice. Zhao, Z. et al., Cell reports 13, 1692-1704 (2015). This dramatic effect in mouse may be due to induction of both lesions in HSC; in humans this type of selection by acquisition of TET1 and TET3 mutations does not occur alone or with TET2$^{MT}$. Another interesting finding, further supporting our central hypothesis, emerged from our comprehensive mutational analysis demonstrating that TET2$^{MT}$ is mutually exclusive with IDH1/2$^{MT}$. Hirsch, C. M. et al., Leukemia 32, 1751-1761 (2018) Indeed among 485 TET2MT cases from our cohort of 1809 MDS patients, only 9 carried IDH1/2$^{MT}$(4 were sub clonal with very small clones) and among 157 IDH1/2$^{MT}$ cases, there were only 11 TET2$^{MT}$ (n=9; p=0.55×10$^{-8}$) of which 5 were non-deleterious missense variant outside of catalytic domain or had low VAF (FIG. 1A). Makishima, H. et al., Nature genetics 49, 204-212 (2017) Additional analysis of TCGA data set of 187 and the recently published "beat AML" cohort of 608 AML patients showed a similar pattern with 4.6 vs 15% of TET2$^{MT}$ within IDH1/2$^{MT}$ or IDH1/2$^{WT}$ cases. Tyner, J. W. et al., Nature 562, 526-531 (2018) Loss of TET2, as a major DNA dioxygenase in HPSC, leads to their critical dependence on TET1/TET3. Neomorphic IDH1/2$^{MT}$ in such a scenario may result in the inhibition of TET1/3 and natural synthetic lethality to TET2$^{MT}$ HSPCs due to the "natural" 2HG. To further support the theory that 2HG, a natural TET2 inhibitor, shows selective toxicity to TET2$^{MT}$ clones, we transduced TET2$^{MT}$ cell line with a vector containing IDH1$^{R132C}$ or IDH2$^{R132H}$ with an inducible tet-on promoter (FIG. 1B). Following induction, cells transduced with mutant vectors died while IDH$^{WT}$, continued to grow (FIG. 1F). The death of TET2$^{MT}$ cells were due to over production of 2HG as determined by LCMS/MS. In agreement with these results, myeloid neoplasm evolution is also inhibited in tet1$^{-/-}$tet2$^{-/-}$ mice and combined loss of tet1$^{-/-}$/tet2$^{-/-}$/tet3$^{-/-}$ in a zebra fish model system results in loss of HSPCs. Dawlaty, M. M. et al. Developmental cell 29, 102-111 (2014). In sum, TET2$^{MT}$ are mostly loss-of-function hits, indicating that TET2 is a bona fide tumor suppressor gene. While the presence of biallelic TET2 inactivation (microdeletions, UPD, biallelic mutations) verifies the gene dose effect, our observations further support that transient inhibition of the residual DNA dioxygenase activity with highly specific potent small molecule inhibitors, modeled on substrate binding active site of TET enzyme is indeed a rational strategy for eliminating TET2-deficient clones. Our underlying hypothesis explaining the selective synthetic lethality approach for TET2$^{MT}$ cells is presented in FIG. 5B.

Proof of principle for TET2 inhibitors. In preparation for this proposal we have established analytic base, generated series of TETi and conducted proof of concept, cell-free, in vitro and small scale in vivo experiments. We optimized assays to assess the impact of mutations or TETi; two independent methods for the hmC/mC quantification were deployed: i) dot blot and ii) a highly sensitive 2D-UPLCMS method. These methods were used to determine the relative TET2 activity in patient's cells with various types of TET2$^{MT}$, in genetically modified (retrovirally-transduced TET2 shRNA) K562 and MOLM13 cells, and cell lines with natural TET2$^{MT}$ and marrow from tet2$^{-/-}$ or tet$^{+/-}$ mice.

Figure 7A:
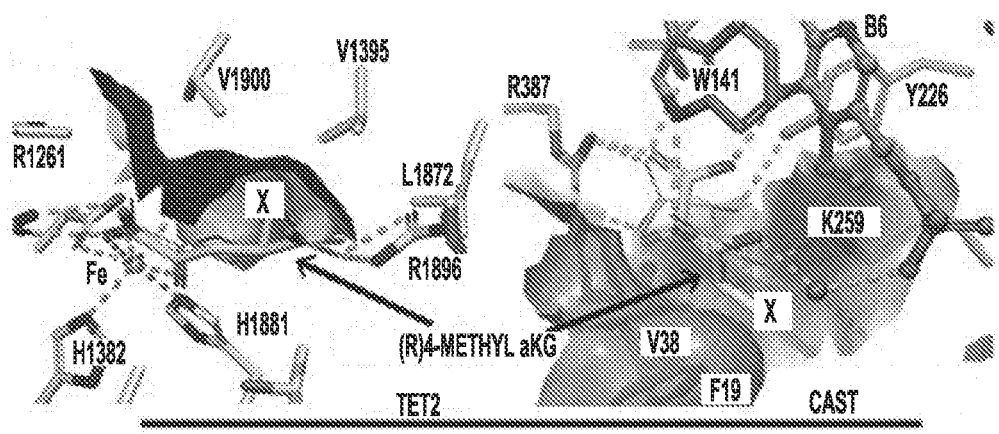
FIGS. 7A and 7B provide an image and schematic representation showing the structure-guided design of TS. (A) Binding models of (R)4-methyl αKG (yellow) with TET2 and cAST, binding sites of the proteins close to the 4-methyl group (denoted by X) are shown in surface representation. (B) Other TETi that design based on these models. Amino acid (AA) residues and the ligand involved in the interactions are as labeled. The C, N and O atoms are shown as white, blue and red, respectively. H-bond and Fe-AA interactions are shown as cyan and purple dashed lines. Ligands from the crystal structures are shown in green line models for comparison. Docking was performed by Glide in Schrodinger Maestro pipeline.
Figure 7B:
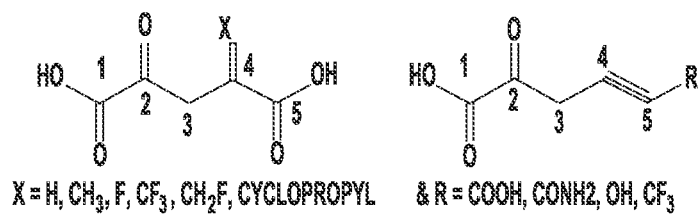

Generation of TET inhibitors. Based on the binding mode of the pseudo-substrates in the TET complex we performed in-silico analyses by free energy perturbation methods using FEP$^{+15}$ and ligand plot analysis using LigPlot$^+$-v.1.4 for αKG and various analogs in the catalytic site and generated several classes of stereo-specific compounds (FIG. 1A, 1B and FIG. 7A). Hu, L. et al., Nature 527, 118-122 (2015). Initial studies focused on derivatives with informative modifications at C-4, and C3-C4 which can be modified with substituents to increase specificity for TET specific active site. As evident from the crystal structure, the cofactor binding site has very limited but unique chemical space. Therefore, our initial design is focused on the pseudo substrate scaffold and later we will expand this space utilizing Schrodinger Maestro pipeline running on a Quantum TXR411-0128R GPU system. We have synthesized various derivatives including C3-C4 alkenyl/alkyny derivatives. These analogs were prepared in 2 different forms one as dilithio salt for in vitro dimethylester for in vivo studies (FIG. 2C). An initial set of scaffolds is presented in FIG. 2G with TETi activity in invitro assays for selected TETi's, 2HG and DMF (FIG. 2C). These results indicate that better binding TETi can be identified and optimized using various biochemical and biophysical approaches to establish structure activity relationship of specific TET inhibition.

Efficacy and specificity of TETi. We used established tet2$^{+/-}$ vs. tet2$^{-/-}$ mouse models as well as several human myeloid cell lines selected to harbor TET2$^{MT}$ or to express low level of TET2 to determine the specificity, establish the read out and provide proof of concept for the proposed strategy. Using suspension and colony cultures followed by the determination of TET2 activity we showed that TET2 deficiency increased proliferation and decreased hmC dioxygenation. Most significantly, TETi were effective in growth suppression, an effect that was dependent on the expression and activity of TET2 (FIG. 3); MOLM13 (IC$_{50}$ 9.6 μM) and SIGM5 (IC$_{50}$ 11.2 μM) with least TET2 expression were most sensitive against to TETi76 (FIG. 3) whereas high TET2 expressing, K562 and HEL01 showed the lowest sensitivity to TETi76 treatment. The IC$_{50}$ of different cells against TETi76 is inversely correlated with TET-activity (FIG. 3). To further probe specificity of TETi76 and its IC$_{50}$ correlation, we knocked-out TET2 from K562 cells and performed a colony forming assays in the presence/absence of TETi76 (FIG. 3).TET2$^{KO}$ sensitized these cells to TETi76 otherwise resistant.

To further validate the feasibility of our proposed strategy as a therapeutic principle, we used mixing experiments in which tet2$^{MT}$/tet2$^{WT}$ were co-cultured at fixed ratios to mimic evolving tet2MT clone and the differences in isoform fractions served as read out. In long-term culture of normal marrow from B6Cd45.1 Pep Boy vs. B6CD45.2 mice of tet2$^{+/-}$ and tet2$^{-/-}$ genetic background. Marrow cell from 3 mice/group were cultured in 1:2 ratio of tet2$^{MT}$/tet2$^{WT}$ with/without TETi. Over the period of culture TETi effectively eliminated otherwise dominating tet2$^{+/-}$ cells (FIG. 4). As expected, tet2$^{MT}$ grew at faster rate in the controls as reflected in the increased ratio >1:1 of tet2$^{MT}$/tet2$^{WT}$, while TETi treatment selectively eliminated the tet2$^{MT}$ cells as determined using CD45.1/CD45.2 surface markers on tet2$^{WT}$ and tet2$^{MT}$ bone marrow, respectively (FIGS. 4A&B). These results indicate that TETi selectively eliminates tet2$^{MT}$ (FIG. 4C). In addition, TETi showed only a minimal effect on normal CD45.1 tet2WT HSPCs (FIGS. 4A&B). In vivo efficacy of TETi. To determine the efficacy of TETi in eliminating tet2$^{MT}$ clones in vivo, we performed a pilot experiment to test the efficacy of our lead compound, TETi76 in murine model system. First we determined MTD utilizing a dose escalation in a group of 3 mice each. Each group received 5 days a week either vehicle or TETi in a weekly dose increments. The MTD was determined at 168 mg/kg. For this dose no mortality were observed in 3 mo. Once the dose was established, B6 Cd45.1 Pep Boy mice (4 mice/group, 2 male, 2 female) was irradiated with a 2×4.8 grey separated by 4 h, a total of 9.6 grey of radiation followed by transplant of 2×10$^6$ cells derived from bl6 Cd45.2 tet2$^{MT}$ (tet2$^{+/-}$ and tet2$^{-/-}$) and tet2$^{WT}$ mice in the ratio of 1:2. Cells from B6 Cd45.1 Pep Boy mice were used as tet2$^{+/+}$ control in the mixing experiment. Once mice were fully recovered as determined by their weight, the ratio of tet2$^{MT}$ and tet2$^{WT}$ marrow was confirmed by CD45.1/CD45.2 cytometry prior to treatment. Each mice were treated with 80 mg/kg 5 days/week. Ratio of CD45.2 vs. CD45.1 was determined at different time points (FIGS. 4D&E). TETi selectively restricts the growth of tet2$^{MT}$ clones in vivo while there has been no impact on the growth of tet2$^{+/+}$ bone marrow. The effect of TETi76 was most pronounced against tet2$^{-/-}$ compared to tet2$^{+/-}$ genotype (FIG. 4). Examples of candidate screening using TET2-deficient MOLM13 is shown including antiproliferative effects and decrease in hmC content. By comparison the effects of natural TETi 2HG are also shown (FIG. 2H). We anticipate that there may be a differential sensitivity of cells to TETi depending on the status TET2 inactivation. Ultimately, we believe that we will be able to identify most effective TETi with a greatest therapeutic window as compared to wild types cells and normal CD34$^+$ cells. Culture of mixed tet2$^{+/-}$tet2$^{-/-}$ and tet2$^{+/+}$ mouse derived marrow cells serving as model of CHIP should show that TETi lead to retraction of tet2$^{KD}$/tet2$^{KO}$ cells. We anticipate that there would be a clinically actionable therapeutic index for TETi. Research Methods SA1: Design, synthesis and functional analysis of TETi: Based on results of in silico modeling a library of 100 TETi will be designed, synthesized and tested in cell-free TET2 for generation of 5 hmH measured by dot blot and LCMS/MS as a readout. TETi will be also tested against recombinant purified TET1, TET2 and TET3. Selected substrates will be further modified to ester or amide, forms to optimize membrane permeability, solubility to provide desired pharmacology. Our preliminary goal for these derivatives is to determine structure activity relationships of substituent (C-4 and C-3) effects. Most of the chemistry procedures for the synthesis of compounds to be included in our studies have already been optimized (FIG. 6B) or are well described in the literature. We will generate several TETi and their esterified forms for in vitro and in vivo use.

SA2: Study the effects of TET-inhibitors in vitro. Analysis of TETi effects will include in primary cells and experimental models. Experimental readout will include 1) proliferation rate, 2) phenotypic change (differentiation by flow or deep whole RNA NGS.) 3) DNA content of 5mC, 5hmC, 5fmC and 5caC by LC-MS/MS or dot blot as previously demonstrated. The following culture system will be used for testing: TET2 shRNA transduced cell lines including K562$^{TET2KD}$ K562$^{TET2KO}$ and U935$^{TET2KD}$, MOLM13$^{TET2KD}$ generated by retroviral transfer of TET2 shRNA and by CRISPR-Cas9. We will also use natural TET2$^{MT}$ cell lines SIGM5 and OCI-AML5. Methylcellulose and suspension cultures (primary and serial re-plating) TET2 shRNA transduced CD34$^+$ cells with and without TETi. Suspension cultures derived from tet2$^{+/-}$, tet2$^{-/-}$ and tet2$^{+/+}$ control mice performed in the presence of growth factors whereby a mixture 10/90, 30/70 or 50/50 between the KD/KO and WT cells. The differential effects of TETi on these cells will be monitored by CD45.1 and CD45.2 typing. Cells from tet2$^{-/-}$ mice with a fully developed disease will be tested in vitro as described above (FIG. 4). Marrow cells from patients with TET2$^{MT}$ myeloid neoplasia, including those with heterozygous (n=6) and bialleleic/homozygous TET2MT (n=6), samples from patients with TET2$^{WT}$ (n=20; matched for morphologic subtype (high risk vs. low risk MDS, MDS/MPN) and normal marrow (n=6). The therapeutic window and toxicity vs. healthy controls will be determined.

SA3: Characterize TETi effects in tet2$^{+/-}$ disease models and xenografts. We will test preventative effects of TETi tet2$^{+/-}$ and tet2$^{-/-}$ mice. Mice will be given 4.5 grey of radiation to accelerate evolution of disease. From age 6-24 mo. we will collect blood subsequent deep NGS and 5hmC 5hmC or LC-MS/MS. PFS, and OS will be established for each of the 3 experimental arms. NHD13 used as a model will be used as control. Per treatment group, 8 mice will be used. As a model for CHIP (or evolution) we will perform competitive transplantation of tet2$^{+/-}$, tet2$^{-/-}$ mouse with tet2$^{+/+}$ mixture at 10-50% of tet2-deficient cells. The expansion kinetics of tet2deficient cells will be monitored using CD45.1 or CD45.2 isotype typing. We will also test the therapeutic effect of TETi in models of established TET2$^{MT}$ MDS. Genetically engineered tet2$^{+/-}$, tet2$^{-/-}$, NHD13, NHD13/tet2$^{+/-}$ and flt3ITD/tet2$^{+/-}$ mice will be cared for until they develop myeloid neoplasia. Leukemic cells will then be harvested and syngeneic recipients will be inoculated with 3 different cell doses (10$^5$-10$^7$) to consistently generate disease. For xenograft experiments we will use samples with TET2 inactivation and irradiated NOD-scidIL2Rg (NSG) mice. Patient MDS isolates will be inoculated i.v. into recipient mice (n=8 per group). We already generated 3 TET2$^{MT}$ and 4 with TET2$^{WT}$ xenografts. Engraftment will be determined by flow cytometry. After signs of disease, spleens will be harvested and analyzed for the presence of neoplastic cells. We aim at generation of "a cohort" of 12 mice (12 TET2$^{MT}$ and 12 TET2$^{WT}$) each carrying a different PDX. Moreover, we will also use natural cell lines with TET2MT (OCI-AML3, SIGM5 and MEG01 see or TET2$^{WT}$). NSG mice will be implanted s.c. bilaterally or injected i.v. Readout will include size of the tumor over time with and without treatment.

Example 2: Synthesis of TET2 Modulators

Figure 5B:
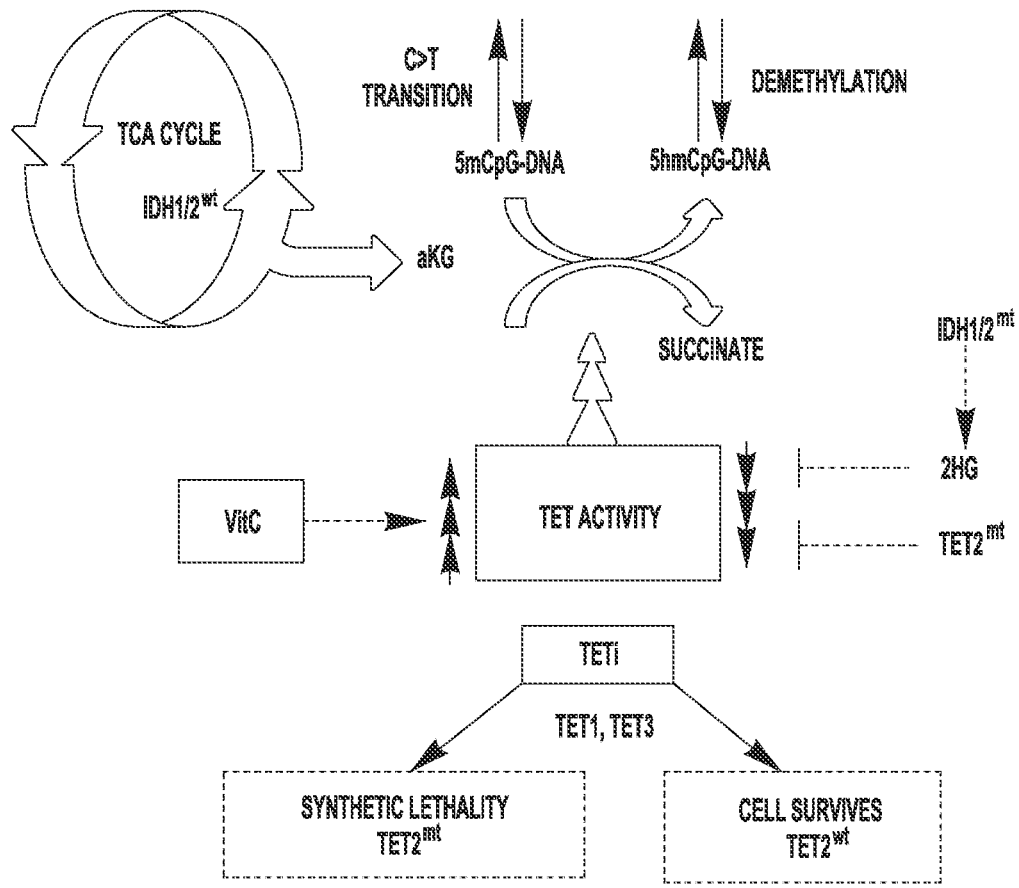

TET2$^{MT}$ are mostly loss-of-function hits, so TET2 is a bona fide tumor suppressor gene (TSG). The presence of somatic microdeletions and uniparental disomy (UPD) with a homozygous TET2$^{MT}$ substantiates the gene dose effect of TET2 lesions. Tet2 knockout mice develop mild anemia, monocytically-skewed, myeloproliferative neoplasia that progress faster in tet2$^{-/-}$ vs. tet2$^{+/-}$ mice. Moran-Crusio et al., Cancer Cell, 20(1):11-24 (2011). LSK cells of such mice display growth advantages in competitive repopulation assays. Lindner et al., Br J Cancer, 100(8):1287-91 (2009). That myeloid neoplasia evolution is inhibited in tet1$^{-/-}$ tet2$^{-/-}$ mice4 suggests that inhibiting tet1 is a reasonable strategy for eliminating tet2$^{-/-}$ clones. TET2 dioxygenase hydroxylates mC in DNA to hmC that prevents maintenance methylation. Li et al., Blood, 118(17):4509-18 (2011). It also further oxidizes hmC in DNA to fC and caC, which are eliminated via base excision repair (BER). Loss of TET2 may cause a slight amount of 5 mC accumulation globally that may slightly increases C>T mutation rates via cytidine deamination (FIG. 5B).

TET2 reactions require a radical equivalent to abstract a hydrogen atom from 5 mC. TET2 obtains this by cleaving the O—O bond of $O_2$. For this it uses 2 electrons gained by decarboxylating αKG and via a $Fe^{2+}/Fe^{3+}$ redox reaction, in two single-electron transfers (to produce a radical intermediate), it 2 electrons possibly obtained from vitC as a cofactor. At the heart of TET2 is a redox cycling $Fe^{2+}/Fe^{3+}$ that stores and utilizes single-electrons allegedly delivered by vitC. Our results with purified recombinant TET2 support the notion that vitC increases the activity of wild-type TET2, unhindered by the presence of TET2$^{MT}$ proteins.

Our hypothesis is that the activity of the wild type allele of TET2 can be restored to overcome haploinsufficiency created by the monoallelic mutation, thereby protracting clinical disease onsets. Such αKG analogs could bypass the inhibitory effects of cellular metabolites such as 2-hydroxyglutarate (2HG) created by IDH1/2 mutations (FIG. 5B), and/or those of succinate or fumarate present in all cells. We refer hereafter to such αKG analogs as turbosubstrates (TS), acknowledging that apparent increases might be achieved via less consumption by other αKG-using enzymes, and thus higher concentrations of TS vs. αKG, as opposed to higher intrinsic reaction rates. As TS strategies are not expected to be applicable to homozygous mutants, we propose instead that in such cases inhibition by a highly specific small molecule inhibitor of TET1 may be useful to achieve synthetic lethality. TET2 has two homologs, TET1 and TET3, and experiments in a murine model have shown that loss of both Tet2 and Tet1 extends life substantially relative to Tet2 loss alone. Jankowska et al., 113(25):6403-6410 (2009). We will thus design and synthesize novel TET1 inhibitors. These compounds, and TET2 TS with and without VitC, will be tested in cell-free, ex-vivo and in in-vivo systems (FIG. 5B). Small animal models will then be used to test these agents in both preventative and therapeutic modes. Our goal is to predict not only clinical outcomes but also molecular parameters such as rates of subclone evolution. Compounds developed could have a broader subsequent impact on cases with mutations in IDH1/2 and KDM6A, which similarly demethylates histones.

The large size of this cohort enabled a more intricate analysis of the distribution of mutations among disease sub entities and determination of the rate of hemizygous, homozygous and biallelic mutations (30% of all mutant cases, 50% in CMML). Analysis of the mutations showed that 47% were frameshifts leading to various truncations and of 20% of missense mutations 88% were located proximal to the active site. Configurations of biallelic mutations included 2 frameshift alterations in 110/557 (~20%) and 2 missense mutations in 7% of cases; only 11% of mutant cases showed homo/hemizygous TET2 truncation mutations. Using exome sequencing data available for 350 cases, we analyzed the clonal hierarchy of TET2$^{MT}$ cases. TET2$^{MT}$ had the highest VAFs, and were thus ancestral, in 65% of patients. Most TET2$^{MT}$ are heterozygous or biallelic involving at least one missense mutation, some of which could be rescued by TS, i.e., in addition to elevating the activity of wild type alleles, in some cases it may also be possible to increase the activity of certain point mutations within the active site of TET2. Cases with biallelic TET2$^{MT}$ wherein neither hit is rescuable should be amenable to TET1 inhibition to achieve synthetic lethality or lineage-changing effects.

One important conclusion of our preliminary studies is that MDS often begins with an ancestral TET2$^{MT}$ prior to MDS onset, and reciprocally, that TET2-mutated MDS often originates from CHIP. While one can calculate that only a minority of TET2 CHIP cases end up with MDS, due to incomplete penetrance, CHIP carriers have been reported to have very high risk of hematological malignancies and thus, presumably, also of MDS, though to prove this one may need to account for attrition by cardiovascular mortality, which increases not only with age but also with CHIP30. These observations suggest that there should be a role for preventive measures in CHIP individuals, and that such measures should be of low intensity, such as the use of mild compounds (namely vitC and (KG analog TS) that gently increase TET2 activity following hypomorphic TET2$^{MT}$.

Impact of the Loss of TET2 Activity on TET2 Products in Human and Murine Cells

We optimized assays to assess the impact of mutation or haploinsufficiency on dioxygenase activity in our laboratory. We deployed 2 independent methods for the quantification of hmC/mC. First, a semi quantitative method of dot blot and second a highly sensitive 2D-UPLCMS method. These methods were used to determine the relative activity of TET2 enzymatic function. We can quantify TET2 dioxygenase activity products in cell lines and patient's bone marrow cells with various types of TET2$^{MT}$ (FIG. 3E) in genetically modified (retrovirally-transduced TET2 shRNA) K562 and MOLM13 cells and bone marrow from Tet2$^{-/-}$ and Tet$^{+/-}$ mice. As expected, haploinsufficiency of TET2 leads to gene-dose dependent decreases in 5hmC and further oxidized products. As evidence that we can measure these endpoints, we showed that in Gulo$^{-/-}$Tet2$^{+/-}$ cells, treatment with vitC increases levels of the TET2 product hmC.

Genomics of TET2 Mutations

We have analyzed a large cohort of approximately 5,000 patients with myeloid neoplasms and have identified 1200 cases with somatic TET2 mutations; the total number of clonally expanded mutations found in TET2 was 1781. Marrow and blood samples from a substantial fraction of these patients are available to us in our clinically annotated IRB-approved sample repository.

Synthetic αKG Analogs Restore the Function of TET2 In-Vitro

LC-MS/MS was used to measure mC to hmC conversion in the presence of αKG in cell free systems with a recombinant TET2 catalytic domain. This assay yielded that vitC increases TET2 activity in a 1:1 mixture of TET2$^{WT}$ with catalytically dead TET2$^{R1896S}$ mutants. This LC-MS/MS assay, and dot blots described previously, will be used in our research to quantify the effects of TET2 TS and TET1 inhibitors. Based on the binding mode of the pseudo substrate in TET2 complex we performed in-silico analyses by free energy perturbation methods using FEP+ (Schrodinger Inc.) and ligand plot analysis using LigPlot+− v.1.4 for α-KG and various analogs in the catalytic site and generated several classes of stereo specific compounds (FIG. 2). Initial studies focused on the syntheses of derivatives with informative modifications at C-4, and C3-C4 which can be modified with substituents that make it more efficient and specific for TET2. We synthesized various C4 derivatives including C3-C4 alkenyl and alkynyl derivatives according to the synthetic scheme shown in FIG. 6B. The C-4 methyl analog was prepared as a dimethylester and as a dilithio salt for in vitro analyses. An initial set of scaffolds is presented in FIG. 2G with agonistic and inhibitory activity in cell-free TET2 activity assays for selected; cell-free titration curves were established and used. Analogous experiments have been performed with the inhibitory αKG analogues and TETiAD along with the known inhibitors 2-HG and DMF used as controls (FIG. 2H). We will determine if a better binding substrate is a better activator in a thermophoresis-based binding assay coupled to our established activity assay.

Scientific Premise

TET2$^{MT}$ belong to one of the most important molecular defects in myeloid neoplasia and are interwoven in metabolic cascades that are affected by other mutations in other genes. Deconvolving this conundrum is a major challenge and of utmost important in MDS research. There is also the issue of further understanding the dependence upon αKG of several other dioxygenases that have been implicated in the pathogenesis of myeloid neoplasia. This work will shed light on this as well. Evidence that has accumulated over this decade and our preliminary data form a strong foundation for our proposed endeavors. TET2 insufficiency due to mutations, deletions (i.e. mostly frame-shifts), and as of yet unexplored, the cellular metabolites succinate and fumarate that are natural product-feedback inhibitors of TET2, are likely key events both in CHIP and in MDS derived from CHIP. We demonstrated that TET2 defects offer an opportunity for metabolic intervention with either TET1 inhibitors or TET2 TS. It is possible to design small molecules based on an αKG scaffold. For TS, there is rational for using them with ascorbic acid. We have shown that suitable experimental models can be established and manipulated in vitro and in vivo to test the potential utility of proposed strategies in preclinical settings. Objective measures of TET2 activity, including not only hmC but also neoplastic growth and mouse survival times, can be reliably quantitated.

Example 3: Design, Synthesis and Functional Analysis of TS and TETi

Anticipated results: We have produced purified recombinant TET2-full-length and catalytic truncated forms of TET2$^{WT}$ and several catalytic inactive mutant proteins TET2$^{R1896}$, TET2$^{R1896M}$, TET2$^{R1896S}$ and TET2$^{S1898F}$. These will be used in cell-free systems to study heterozygous and homozygous mutation configurations. Based on results of in-silico modeling a library of 20-25 αKG analogs will be prepared and tested in cell-free TET2 activity assays. Selected substrates will be further modified to ester, amide, or other prodrug forms to optimize membrane permeability, solubility, and provide desired pharmacology. The more active compounds will be prepared in pure chiral (R or S) forms. Our preliminary goal for these derivatives is to determine SAR (Structure Activity Relationships) of substituent effects on TET2 enzyme activity. Primarily, we will focus on appropriate C-4 and some C-3 substituents on the αKG backbone as these should not interfere with $Fe^{2+}$ and $O_2$ binding during the Tet2 catalytic cycle. Our set of compounds to be synthesized is based on free energy perturbation using Schrodinger FEP+ software (Schrodinger Inc.) running on a Quantum TXR411-0128R GPU system in Schrodinger Maestro environment. Most of the chemistry procedures for the synthesis of compounds to be included in our studies have been already optimized or are well described in the literature. We envision that our comprehensive SAR studies will yield compounds that provide selective activation of TET2 enzymes generated by the remaining TET2WT allele and other compounds that selectively inhibit TET1.

Figure 8:
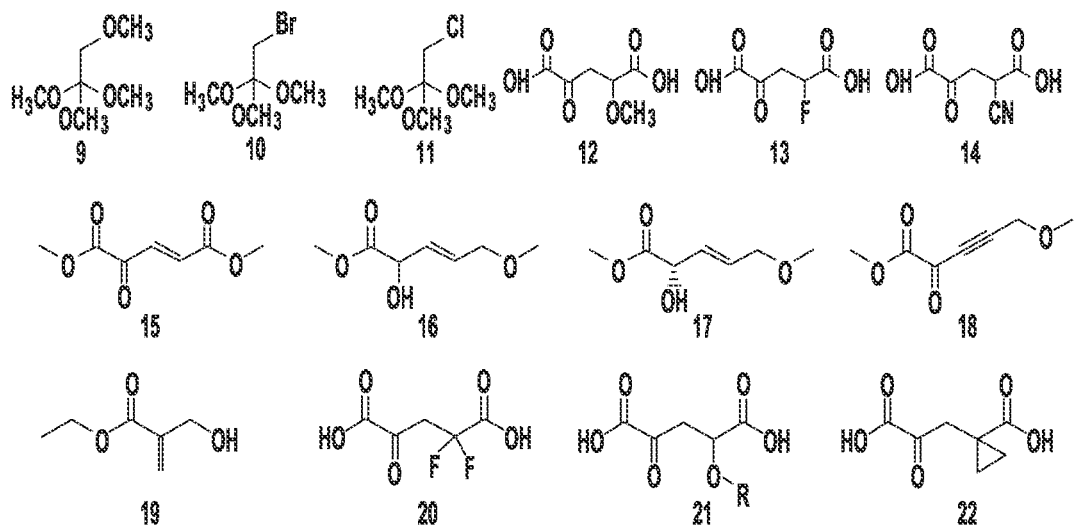
FIG. 8 provides a scheme showing the structure-guided TS design, and examples of some of the fragments used in the synthesis of TET2.

Specific procedures: αKG analogs that bear various C-4 alkyl substituents ($CH_3$, $-CH_2CH_3$, $-CH_2CH_2CH_3$, etc.) will be prepared according to the scheme presented in FIG. 8. Sebastien et al., J. Med. Chem. 48, 7980-7992 (2005). Bayliss-Hillman reaction between methyl acrylate 1 and acetaldehyde 2 in the presence of DABCO allows large scale preparation of the key intermediate methyl 2-(1-hydroxyethyl)acrylate 3. Ortho esters 4 which are either commercially available or prepared from the corresponding nitriles using the Pinner method are then reacted with 3 under acid catalysis and undergo a stereoselective Claisen-Johnson rearrangement leading to dimethyl 2-ethylidene-4-alkylglutarate derivatives 6. We have already prepared several C-4 substituted 2-keto esters 7 and the corresponding substituted lithium 2-ketoglutarates 8 via oxidative cleavage with sodium periodate in the presence of a catalytic amount of ruthenium peroxide followed by ester hydrolysis with lithium hydroxide. We anticipate that other C-4 derived SAR informative derivatives (such as 12-14) using the same protocols can be made from commercially available ortho esters 9-11. Furthermore, since the orthoester Claisen-Johnson rearrangement has been shown to be stereoselective, following presented in FIG. 8 using either enantiomer of key intermediate 3 should provide optically enriched or pure C-4 substituted αKG analogues. Rodney et al., Eur. J. Org. Chem., 1047-1055 (2012). Chiral preparation of alcohol 3 has been described. U.S. Pat. No. 5,241,064A. We have already prepared C-3 unsaturated αKG analogues following scheme 1 by reaction of methyl 2-(1-hydroxyethyl)acrylate 3 with ortho ester 11 to give 15 (tet 2 inhibitor) after facile elimination of the C-4 chloride. Other unsaturated derivatives of interest (such as 16, 17, and 18) can be prepared by procedures described by Bonnaffe et al. or Wong et al. Bonaffe D and Simon H., Tet, 48, 44, 9695-9706 (1992); Wong et al., J. Org. Chem., 66, 3606-3609 (2001). Of interest to our studies is the synthesis of some αKG derived compounds 20-22 via metal-mediated allylation reactions of bromide 19. Liu et al., Org. Lett., 13, 11, 2924-2927 (2011).

Example 4: Separation of TETi76 Isomers

TETi76 (a.k.a. AD145) was dissolved in 50 mL 1,2 dichloroethane followed by the addition of N, N-diisopropylethylamine and 4-DMAP. Keep stirring at 0° C. and camphenic acid chloride was added portion wise at 0° C. to the reaction mixture. Check a TLC after 2 h for the progress of the reaction. Reaction were completed in 12 h check by the TLC in 20% EtOAc:Hexane. Two new spot appeared above the TETi76 in the permanganate staining. Solvent were evaporated under reduced pressure and residue was dissolved in EtOAc (300 mL), washed with brine twice (50 mL) followed by the HCl (10%) washed twice (50 mL each). Final brine washed again and organic layer dried over the sodium sulfate, filtered and solvent were evaporated under reduced pressure.

The cure was purified over the flash column that was 16' silica length with 0.5 diameter for 24/40 column for 5 g crude. Flash column has done with very patiently on 1 atm added the crude and left for the overnight to settle down. Then use the hexane about 1 L first only then increase the ethyl acetate gradient till 7% the both spot can come down with 7% EtOAc:Hexane and can collect the fraction in 15 mL each check the TLC with stain of potassium permanganate. NMR analysis showed that four distinct diastereoisomers had been purified. The purification of TETi76 diastereoisomers is further supported by the reaction scheme and table of reactants and products shown below.

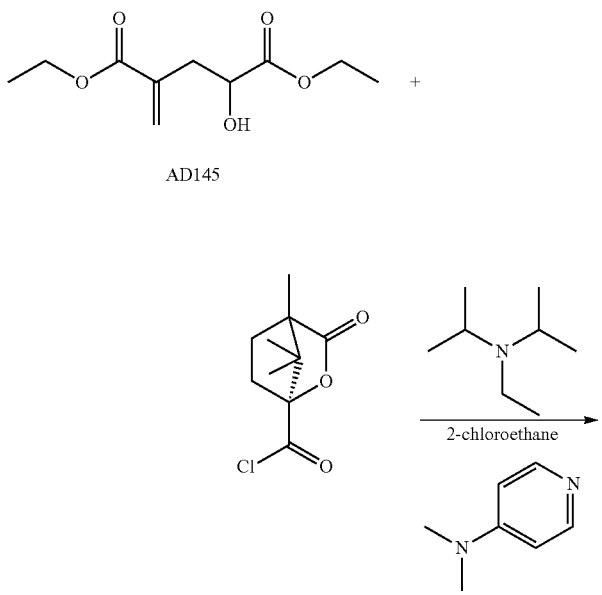

AD145

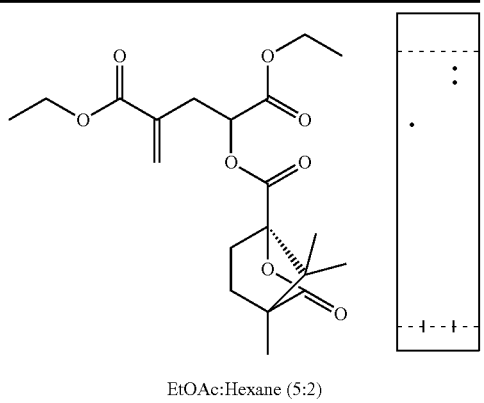

EtOAc:Hexane (5:2)

| Reactants | | | | Products | |
|---|---|---|---|---|---|
| Formula | $C_{10}H_{16}O_5$ | $C_{10}H_{13}ClO_3$ | $C_8H_{19}N$ | $C_7H_{10}N_2$ | Formula | $C_{20}H_{28}O_8$ |
| MW | 216.23 | 216.66 | 129.25 | 122.17 | MW | 396.44 |
| Limiting? | Yes | No | No | No | Equivalents | |
| Equivalents | 1.00 | 1.10 | 1.50 | 0.10 | % Completion | |
| Sample mass | 2.75 g | 3.03 g | 2.47 g | 155.37 mg | Expected Mass | 5.04 g |
| % Weight | | | | | Expected Moles | 12.72 mmol |
| Molarity | | | | | Measured Mass | |
| Density | | | 740.00 mg/mL | | Purity | |
| Volume | | | 3.33 mL | | Product Mass | |
| Reactant Moles | 12.72 mmol | 13.99 mmol | 19.08 mmol | 1.27 mmol | Product Moles | |
| Reactant Mass | 2.75 g | 3.03 g | 2.47 g | 155.37 mg | % Yield | |

30

The chemical names of the two TETi76 isomers are diethyl (4R)-methylene-4-((4,7,7-trimethyl-3-oxo-2-oxabicyclo[2.2.1]heptane-1-carbonyl)oxy)pentanedioate and diethyl (4S)-methylene-4-((4,7,7-trimethyl-3-oxo-2-oxabicyclo[2.2.1]heptane-1-carbonyl)oxy)pentanedioate.

The complete disclosure of all patents, patent applications, and publications, and electronically available material cited herein are incorporated by reference. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

What is claimed is:

1. A method of treating cancer in a subject in need thereof by administering a therapeutically effective amount of a compound of Formula I:

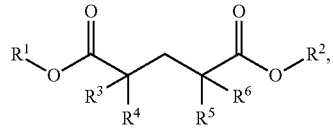

(I)

wherein R¹ and R² are independently selected from $CH_3$, $CH_2CH_3$, and $C_1$-$C_6$ alkyl, R³ is H and R⁴ is —$CH_3$, or R³ and R⁴ are combined to form =$CH_2$ or a cyclopropyl group; and R⁵ and R⁶ are independently selected from H, halogen, —OH, —$CF_3$, and $C_1$-$C_6$ alkyl, or R⁵ and R⁶ are combined to form =O;

or a pharmaceutically acceptable salt thereof selected from the group of salts consisting of chloride, bromide, nitrate, ammonium, sulfate, tosylate, phosphate, tartrate, ethylenediamine, and maleate salts.

2. The method of claim 1, wherein the compound is a compound selected from the group consisting of

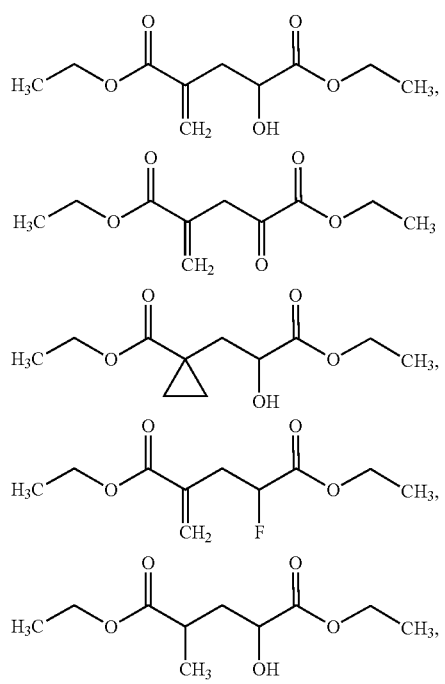

-continued

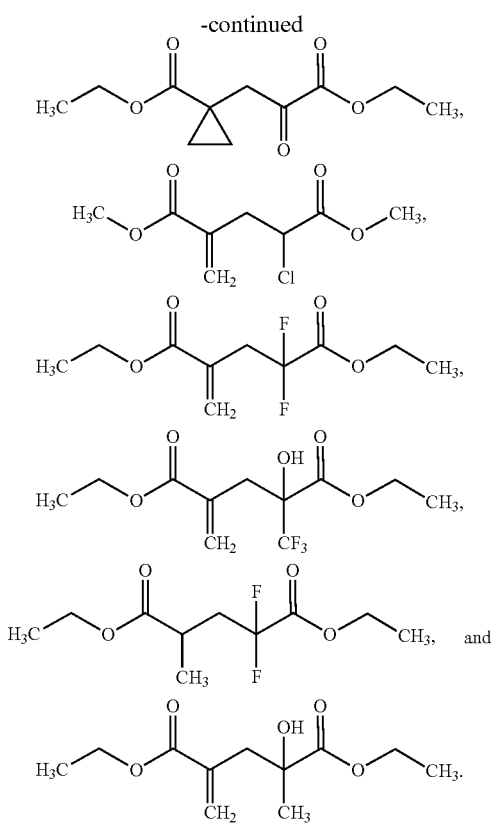

3. The method of claim 1, wherein the compound is

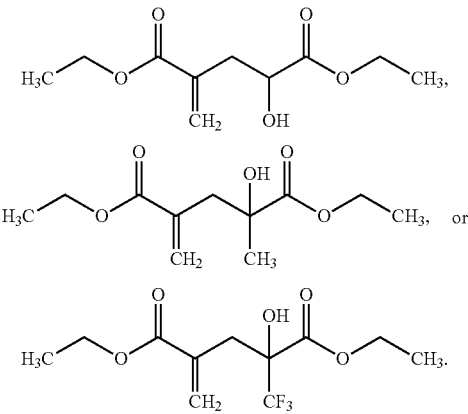

4. The method of claim 1, wherein the compound is administered together with a pharmaceutically acceptable carrier.

5. The method of claim 1, wherein the cancer is a cancer having a TET2 mutation.

6. The method of claim 1, wherein the cancer is selected from myelodysplastic syndrome, myeloproliferative neoplasm, and acute myeloid leukemia.

7. The method of claim 1, wherein the subject is human.

* * * * *